United States Patent
Goldenheim et al.

(10) Patent No.: US 6,534,081 B2
(45) Date of Patent: *Mar. 18, 2003

(54) PROLONGED ANESTHESIA IN JOINTS AND BODY SPACES

(75) Inventors: Paul Goldenheim, Wilton, CT (US); Donna Donigi-Gale, Richfield, CT (US); Richard Sackler, Greenwich, CT (US); Peter Lacouture, Newton, CT (US); Mark Chasin, Manalapan, NJ (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 09/824,465

(22) Filed: Apr. 2, 2001

(65) Prior Publication Data

US 2002/0054915 A1 May 9, 2002

Related U.S. Application Data

(63) Continuation of application No. 09/109,324, filed on Jul. 2, 1998, now Pat. No. 6,248,345.
(60) Provisional application No. 60/051,601, filed on Jul. 2, 1997.

(51) Int. Cl.[7] .............................. A61F 2/02; A61K 9/50; A61K 47/30
(52) U.S. Cl. ...................... 424/426; 424/501; 424/502; 514/772.3; 264/4.33; 428/402
(58) Field of Search .................. 424/426, 501, 424/502; 514/772.3; 264/4.33; 428/402

(56) References Cited

U.S. PATENT DOCUMENTS

| | | | |
|---|---|---|---|
| 2,174,796 A | 10/1939 | Luzzi | 32/34 |
| 2,835,628 A | 5/1958 | Saffir | 167/84 |
| 3,185,625 A | 5/1965 | Brown | 167/82 |
| 3,337,400 A | 8/1967 | Smith | 167/52 |
| 3,507,952 A | 4/1970 | Rednick et al. | 424/22 |

(List continued on next page.)

FOREIGN PATENT DOCUMENTS

| | | |
|---|---|---|
| CA | 1143289 | 3/1983 |
| DE | 2930248 | 2/1981 |
| EP | 0195906 | 2/1986 |

(List continued on next page.)

OTHER PUBLICATIONS

G. McCleane, M.D., et al., The addition of triamcinolone acetonide to bupivacaine has no effect on the quality of analgesia produced by ilioinguinal nerve block, Anaesthesia, vol. 49, pp. 819–820, 1994.

Naoki Wakiyama, et al., Influence of physiochemical properties of polylactic acid on the characteristics and in vitro release patterns of polylactic acid microspheres containing local anesthetics, Chem. Pharm. Bull, 30 (7), pp. 2621–2628, 1982.

Duncan H. Haynes, Ph.D., et al., Ultra–long–duration Local Anesthesia Produced by Injection Lecithin–coated Methoxyflurane Microdroplets, Anesthesiology, 63:490–499, 1985.

(List continued on next page.)

Primary Examiner—Carlos Azpuru
(74) Attorney, Agent, or Firm—Davidson, Davidson & Kappel, LLC

(57) ABSTRACT

Sustained release local anesthetic formulations are administered intra articularly and/or into body spaces/cavities. The formulation is preferably a plurality of injectable microparticles including a local anesthetic and an effective amount of a biocompatible, biodegradable, sustained release material prolonging the release of the local anesthetic and optionally and a pharmaceutically acceptable, i.e., non-toxic, augmenting agent effective to prolong the duration of the local anesthesia for a time period longer than that obtainable without the augmenting agent.

31 Claims, 1 Drawing Sheet

U.S. PATENT DOCUMENTS

| | | | |
|---|---|---|---|
| 3,535,419 A | 10/1970 | Siegrist et al. | 424/22 |
| 3,736,646 A | 6/1973 | Schmitt et al. | 29/458 |
| 3,755,558 A | 8/1973 | Scribner | 424/47 |
| 3,773,919 A | 11/1973 | Boswell et al. | 424/19 |
| 3,844,285 A | 10/1974 | Laby | 128/260 |
| 3,887,699 A | 6/1975 | Yolles | 424/19 |
| 3,943,063 A | 3/1976 | Morishita et al. | 252/316 |
| 3,972,995 A | 8/1976 | Tsuk et al. | 424/28 |
| 3,972,999 A | 8/1976 | Tsuk | 424/78 |
| 3,976,071 A | 8/1976 | Sadek | 128/260 |
| 3,991,766 A | 11/1976 | Schmitt et al. | 128/335.5 |
| 4,001,388 A | 1/1977 | Shell | 424/14 |
| 4,011,312 A | 3/1977 | Reuter et al. | 424/78 |
| 4,034,758 A | 7/1977 | Theeuwes | 128/260 |
| 4,039,653 A | 8/1977 | DeFoney et al. | 424/19 |
| 4,070,347 A | 1/1978 | Schmitt | 260/77.5 D |
| 4,076,798 A | 2/1978 | Casey et al. | 424/22 |
| 4,089,800 A | 5/1978 | Temple | 252/316 |
| 4,093,709 A | 6/1978 | Choi et al. | 424/19 |
| 4,118,470 A | 10/1978 | Casey et al. | 424/19 |
| 4,131,648 A | 12/1978 | Choi et al. | 424/22 |
| 4,138,344 A | 2/1979 | Choi et al. | 252/1 |
| 4,144,317 A | 3/1979 | Higuchi et al. | 424/21 |
| 4,164,560 A | 8/1979 | Folkman et al. | 424/22 |
| 4,166,107 A | 8/1979 | Miller et al. | 424/19 |
| 4,166,800 A | 9/1979 | Fong | 252/316 |
| 4,175,326 A | 11/1979 | Goodson | 433/80 |
| 4,226,848 A | 10/1980 | Nagai et al. | 424/19 |
| 4,250,163 A | 2/1981 | Nagai et al. | 424/14 |
| 4,276,880 A | 7/1981 | Malmin | 128/221 |
| 4,293,539 A | 10/1981 | Ludwig et al. | 424/19 |
| 4,321,038 A | 3/1982 | Porteous | 433/136 |
| 4,369,172 A | 1/1983 | Schor et al. | 424/19 |
| 4,384,975 A | 5/1983 | Fong | 427/213.36 |
| 4,389,330 A | 6/1983 | Tice et al. | 427/213.36 |
| 4,404,183 A | 9/1983 | Kawata et al. | 424/19 |
| 4,419,340 A | 12/1983 | Yolles | 424/19 |
| 4,434,153 A | 2/1984 | Urquhart et al. | 424/22 |
| 4,479,911 A | 10/1984 | Fong | 264/4.6 |
| 4,530,840 A | 7/1985 | Tice et al. | 514/179 |
| 4,542,025 A | 9/1985 | Tice et al. | 424/78 |
| 4,557,925 A | 12/1985 | Lindahl et al. | 424/19 |
| 4,568,535 A | 2/1986 | Loesche | 424/19 |
| 4,568,536 A | 2/1986 | Kronenthal et al. | 424/22 |
| 4,569,837 A | 2/1986 | Suzuki et al. | 424/28 |
| 4,585,651 A | 4/1986 | Beck et al. | 424/88 |
| 4,597,960 A | 7/1986 | Cohen | 424/28 |
| 4,622,219 A | 11/1986 | Haynes | 424/38 |
| 4,622,244 A | 11/1986 | Lapka et al. | 427/213.32 |
| 4,623,588 A | 11/1986 | Nuwayser et al. | 428/402.24 |
| 4,650,665 A | 3/1987 | Kronenthal et al. | 424/435 |
| 4,652,441 A | 3/1987 | Okada et al. | 424/19 |
| 4,685,883 A | 8/1987 | Jernberg | 433/136 |
| 4,713,244 A | 12/1987 | Bawa et al. | 424/429 |
| 4,716,203 A | 12/1987 | Casey et al. | 525/408 |
| 4,725,442 A | 2/1988 | Haynes | 424/490 |
| 4,735,945 A | 4/1988 | Sakamoto et al. | 514/279 |
| 4,756,907 A | 7/1988 | Beck et al. | 424/85 |
| 4,757,128 A | 7/1988 | Domb et al. | 528/271 |
| 4,767,628 A | 8/1988 | Hutchinson | 424/426 |
| 4,780,320 A | 10/1988 | Baker | 424/493 |
| 4,789,726 A | 12/1988 | Hutchinson | 528/354 |
| 4,801,739 A | 1/1989 | Franz et al. | 560/185 |
| 4,861,627 A | 8/1989 | Mathiowitz et al. | 427/213.31 |
| 4,874,612 A | 10/1989 | Deasy | 424/425 |
| 4,882,168 A | 11/1989 | Casey et al. | 424/468 |
| 4,883,666 A | 11/1989 | Sabel et al. | 424/422 |
| 4,888,176 A | 12/1989 | Langer et al. | 424/426 |
| 4,891,225 A | 1/1990 | Langer et al. | 424/428 |
| 4,892,736 A | 1/1990 | Goodson | 424/435 |
| 4,906,474 A | 3/1990 | Langer et al. | 424/428 |
| 4,919,939 A | 4/1990 | Baker | 424/493 |
| 4,933,182 A | 6/1990 | Higashi et al. | 424/425 |
| 5,000,886 A | 3/1991 | Lawter et al. | 264/4.3 |
| 5,004,602 A | 4/1991 | Hutchinson | 424/78 |
| 5,007,790 A | 4/1991 | Shell | 424/451 |
| 5,013,553 A | 5/1991 | Southard et al. | 424/426 |
| 5,019,379 A | 5/1991 | Domb et al. | 424/78 |
| 5,019,400 A | 5/1991 | Gombotz et al. | 424/497 |
| 5,032,384 A | 7/1991 | Yeh et al. | 424/49 |
| 5,061,492 A | 10/1991 | Okada et al. | 424/423 |
| 5,075,109 A | 12/1991 | Tice et al. | 424/88 |
| 5,084,267 A | 1/1992 | Damani | 424/426 |
| 5,100,669 A | 3/1992 | Hyon et al. | 424/426 |
| 5,114,718 A | 5/1992 | Damani | 424/422 |
| 5,122,367 A | 6/1992 | Ron et al. | 424/80 |
| 5,143,661 A | 9/1992 | Lawter et al. | 264/4.3 |
| 5,188,837 A | 2/1993 | Domb | 424/450 |
| 5,198,220 A | 3/1993 | Damani | 424/426 |
| 5,222,529 A | 6/1993 | Zoltan | 141/4 |
| 5,225,441 A | 7/1993 | Vogel et al. | 514/557 |
| 5,227,165 A | 7/1993 | Domb et al. | 424/450 |
| 5,236,355 A | 8/1993 | Brizzolara et al. | 433/80 |
| 5,252,701 A | 10/1993 | Jarrett et al. | 528/354 |
| 5,264,207 A | 11/1993 | Bommelaer et al. | 424/69 |
| 5,272,139 A | 12/1993 | Cary, Jr. | 514/171 |
| 5,330,452 A | 7/1994 | Zook | 604/307 |
| 5,401,507 A | 3/1995 | Lewis | 424/426 |
| 5,407,609 A | 4/1995 | Tice et al. | 264/46 |
| 5,492,901 A | 2/1996 | Fabunan | 514/171 |
| 5,540,912 A | 7/1996 | Roorda et al. | 424/422 |
| 5,543,156 A | 8/1996 | Roorda et al. | 424/484 |
| 5,618,563 A | 4/1997 | Berde et al. | 424/501 |
| 5,650,173 A | 7/1997 | Ramstack et al. | 424/489 |
| 5,654,008 A | 8/1997 | Herbert et al. | 424/489 |
| 5,700,485 A * | 12/1997 | Berde et al. | 424/501 |
| 5,747,060 A * | 5/1998 | Sackler et al. | 424/426 |
| 5,922,340 A | 7/1999 | Berde et al. | 424/426 |
| 5,942,241 A * | 8/1999 | Chasin et al. | 424/426 |
| 6,248,345 B1 | 6/2001 | Goldenheim et al. | 424/426 |

FOREIGN PATENT DOCUMENTS

| | | |
|---|---|---|
| EP | 0244118 | 11/1987 |
| EP | 0430474 | 6/1991 |
| GB | 2034182 | 6/1980 |
| WO | 9117772 | 11/1991 |
| WO | 9207555 | 5/1992 |
| WO | 9215286 | 9/1992 |
| WO | WO9320138 | 10/1993 |
| WO | WO9405265 | 3/1994 |
| WO | WO9641616 | 12/1996 |

OTHER PUBLICATIONS

Baguley, Bruce C., et al., "Inhibition of Growth of Colon 38 Adenocarcinoma by Vinblastine and Colchicine: Evidence for a Vascular Mechanism", *Eur.J. Cancer*, vol. 27, No. 4, pp. 482–487 (1991).

Castillo, et al., "Glucocorticoids Prolong Rat Sciatic Nerve Blockade in Vivo from Bupivacaine Microspheres", Anesthesiology, 85:1157–66 (1996).

Abstract: Nakano et al., "Biodegradable microspheres for Prolonged Anesthesia", HCAPLUS 102:209896 (1985).

Nakano et al., "Biodegradable microspheres for prolonged local anesthesia," Microspheres and Drug Therapy: Pharmaceutical, Immunological and Medical Aspects, pp. 327–335 (1984).

Kojima et al., "Preparation and Evaluation in Vitro of Polycarbonate Microspheres Containing Local Anesthetics", Chem. Pharm. Bull., 32(7)2795–2802 (1984).

Physicians Desk Reference, "Marcaine", 51 Edition, pp. 2446–2449 (1997).

Mathiowitz, E., et al., "Polyanhydride Microspheres as Drug Carriers. II. Microencapsulation by Solvent Removal", *Journal of Applied Polymer Science*, vol. 35, pp. 755–774 (1988).

Splenlehauer, G., et al., "In vitro and in vivo degradation of poly(D,L lactide/glycolide) type microspheres made by solvent evaporation method", *Biomaterials*, vol. 10, pp. 557–563 (Oct. 1989).

Thies, Curt, "Microcapsules as Drug Devices Systems", *Crit. Rev. Biomed. Eng.*, vol. 8, Issue 4, pp. 335–383 (1982).

Windholz M. et al., *The Merck Index*, 10th Edition, p. 37, Abstract # 225 (1983).

Thomas R. Tice, et al. Biodegradation of Microcapsules and Biomedical Devices Prepared with Resorbable Polyesters, Southern Research Institute, University of Alabama. (pp. 21–23) 1983.

N.H. Shah, et al., A biodegradable injectable implant for delivering micro and macromolecules using poly (lactic-–co–glycolic) acid (PLGA) copolymers, Journal of Controlled Release, 27 (1993) 139–147.

D.L. Williams, Microencapsulated Local Anesthetics, Proc. Int Symp. Rel Bioact Mater, 11:69–070 (1984).

Journal of Dental Research, IADR Abstract Papers, vol. 61, papers 860 and 861, Mar. 1982.

Richard L. Dunn, et al., Monolithic Fibers for Controlled Delivery of Tetracycline, Southern Research Institute (pp. 157–159), 1981.

Thomas R. Tice, Controlled Release of Ampicillin and Gentamicin from Biodegradable Microcapsules, Southern Research Institute, 1981.

Roland Bodmeier, et al., Polylactic microspheres containing quinidine base and quinidine sulphate prepared by the solvent evaporation method. III. Morphology of the microspheres during dissolution studies, J. Microencapsulation, vol. 5, No. 4, pp. 323–330, 1988.

Marshall Devor, et al., Corticosteroids Suppress Ectopic Neural Discharge Originating in Experimental Neuromas, Pain, 22 pp. 127–137, (1985).

Beck, Lee R., et al., "Poly(DL–Lactide–co–glycolide)/Norethisterone Microcapsules: an Injectable Biodegradable Contraceptive", *Biology of Reproduction*, vol. 28, pp. 186–195 (1983).

Bissery, M.C., et al., "A Study of Process Parameters in the Making of Microspheres by the Solvent Evaporation Procedure", EXPO–Congr. Int. Technol. Pharm., 3rd, pp. 233–239 (1983).

Bodmeier, R., et al., "Solvent selection in the preparation of poly(DL–lactide) microspheres prepared by the solvent evaporation method", *International Journal of Pharmaceutics*, vol. 43, pp. 179–186, (1988).

Bodmeier, R., et al., "Polylactic acid microspheres containing quinidine base and quinidine sulphate prepared by the solvent evaporation technique. II. Some process parameters influencing the preparation and properties of microspheres", *J. Microencapsulation*, vol. 4, No. 4, pp. 289–297 (1987).

Hill, S.A., et al., "Vinca Alkaloids: Anti–vascular Effects in a Murine Tumour", *Euro. J. Cancer*, vol. 29A, No. 9, pp. 1320–1324 (1993).

Jalil, R., et al., "Microencapsulation using poly(L–lactic acid) I: Microcapsule properties affected by the preparative technique", *J. Microencapsul.*, vol. 6, No. 4, pp. 473–484 (Oct.–Dec. 1989).

Lin, Shan–Yang, et al., "Insulin Controlled–release Microcapsules to Prolong the Hypoglycemic Effect in Diabetic Rats", *Biomat. Art. Cells, Art. Org.*, vol. 16, No. 4, pp. 815–828 (1988).

Lin, Shan–Yang, et al., "Microencapsulation and controlled release of insulin from polylactic acid microcapsules", *Biomat. Med. Dev., Art. Org.*, vol. 13, Nos. 3&4, pp. 187–201 (1985–86).

Abstract: Le Corre, et al., "Spinal controlled delivery of bupivacaine from DL–lactic acid oligomer microspheres", J. Pharm Sci 1995 Jan. 84(1) 75–78.

Abstract: Yamamoto, et al., "Effects of colchicine applied to the colchicine applied . . . constriction", Pain, Nov. 1993, 55(2):227–33.

Abstract: Gradus–Pizlo, et al., "Local delivery of biodegradable microparticles containing colchicine or a . . . ", J.Am-.Coll. Cardiol. 1995 Nov. 26(6) 1549–57.

Abstract: Penickova V., et al., "Vinblastin iontophoresis in treating intractable pain", Acta Univ Palacki Olomuc Fac Med 1990 128:37–47.

Abstract: Kantner, et al., Regulatory mechanisms for substance P in the dorsal horn during a nociceptive stimulus: axoplasmic transport vs. electrical activity., Brain Res., Oct. 22, 1986 385(2):282–90.

Jaffe, Howard, "Microencapsulation Process", copy of government–owned invention description, Ser. No.: 943,940, filed Aug. 17, 1978, U.S. Department of Agriculture, Hyattsville, MD, 11 pages.

Algire, Glenn H., et al., "Vascular Reactions of Normal and Malignant Tissues In Vivo. VI.. The Role of Hypotension in the Action of Components of Podophyllin on Transplanted Sarcomas", *Journal of the American Cancer Institute*, vol. 14, No. 4, Feb. 1954, pp. 879–893.

CA 125:104914, , Joanne Curley, et al., "Prolonged regional nerve blockade: Injectable biodegradable bupivacaine/polyester microspheres" 1996.

Jean–Marc Malinovsky, et al., "Motor and Blood Pressures Effects of Epidural Sustained–Release Bupivacaine from Polymer Microspheres: A Dose–Response Study in Rabbits", Anesth Analg 1995, 81:519–24.

L.S. Goodman, et al., "The Pharmacological Basis of Therapeutics", Fourth Edition, 1970, The MacMillan Co., p. 372.

Vol. IA "Drug Information for the Health Care Professional", USP DI, 1989, Ninth Edition, Anesthetics (Mucosal–Local), pp. 183–184; 196–197; 201–203.

Setterstrom, Tice, Lewis and Meyers, "Controlled Release of Antibiotics from Biodegradable Microcapsules fro Wound Infection Control", U.S. Army Institute of Dental Research, (1982), 12 pages.

Abstract: Archer DR, et al. "Changes in slow axonal transport of tubulin induced by local application of colchicine to rabbit vagus nerve", Acta Physiol Scand 1994 Jan. 150(1):57–65.

March, et al., "Biodegradable Microspheres Containing a Colchicine Analogue Inhibit DNA Synthesis in Vascular Smooth Muscle Cells", 1994, pp. 1929–1933.

William T. Buchanan, et al. Systemic Effects of epinephrine–impregnated retraction cord in fixed partial denture prosthodontics, JADA, vol. 104, Apr. 1982.

David B. Masters, et al., Sustained Local Anesthetic Release from Bioerodible Polymer Matrices: A Potential Method for Prolonged Regional Anesthesia, Pharmaceutical Research, vol. 10, No. 10, pp. 1527–1532,1993.

Sandrock and Warfield, "Epidural Steroids and Facet Injections", Ch. 29 *Principles and Practice of Pain Management*, Warfield, C.A., editor (McGraw–Hill, Inc. 1993).

Waldman, et al., "The Relief of Body Wall Pain Secondary to Malignant Hepatic Metastases by Intercostal Nerve Block with Bupivacaine and Methylprednisolone", *J. Pain Symptom Management*, 3(1), 39–43 (1988), (see in particular p. 42, col. 2).

Bonica, John J. and F. Peter Buckley, "Regional Analgesia with Local Anesthetics", *The Management of Pain II*; pp. 1883–1966, (1990), Lea & Febiger (Eds.) Second Edition.

Lewis, D.H., et al., "The Use of In Vitro Release Methods to Guide the Development of Controlled–Release Formulations", 9th International Symposium on Controlled Release of Bioactive Maerials, Sponsored by Controlled Release Society, Inc., pp. 61–64.

Masters, D.B., et al., Meeting for the American Society of Anesthesiologists, vol. 75:A680, (1991).

Devor, et al., 1983, "Axoplasmic Transport Block Reduces Ectopic Impulse Generation in Injured Peripheral Nerves", pp. 73–85.

Schnebel, et al., "The Use of Oral Colchicine for Low–Back Pain", 1987, pp. 354–357.

Tice, Thomas R., et al., "Preparation of Injectable Controlled–Release Microcapsules by a Solvent–Evaporation Process", Journal of Controlled Release, 2:343–352 (1985).

Wakiyama, Naoki, et al., "Preparation and Evaluation in Vitro and in Vivo of Polylactic Acid Microspheres containing Dibucaine", *Chem. Pharm. Bull*, 30:3719–3727 (1982).

Duncan, et al., "Treatment of Upper Extremity Reflex Sympathetic Dystrophy with Joint Stiffness Using Sympatholytic Bier Blocks and Manipulation" *Orthopedics* 11(6), pp. 883–886, (1988).

Flanagan, et al., "Intra–articular injection for pain relief in patients awaiting hip replacement", *Ann. Royal Coll. Surg. Eng.*, vol. 70, pp. 156–157 (1988).

Glasser, et al., "The perioperative use of corticosteroids and bupivacaine in the management of lumbar disc disease", *J. Neurosurg.*, vol. 78, pp. 383–387, (1993).

Guttu, et al., "Delayed Healing of Muscle After Injection of Bupivacaine and Steroid", *Annals of Dentistry*, 49:5–8, (1990).

Hall, et al., "Acute effects of intravenous glucocorticoid on cat spinal motor neuron electrical properties", *Brain Research*, vol. 240, pp. 186–190, (1982).

Sato, T., et al., "Porous Biodegradable Microspheres for Controlled Drug Delivery. I. Assessment of Processing Conditions and Solvent Removal Techniques", *Pharmaceutical Research*, 5:21–30 (1988).

Schneider, Markus, M.D., et al., "A Preferential Inhibition of Impulses in C–fibers of the Rabbit Vagus Nerve by Veratridine, an Activator of Sodium Channels", *Anesthesiology*, 74:270–280 (1991).

Miyazaki, S., et al., "External control of drug release: controlled release of insulin from a hydrophilic polymer implant by ultrasound irradiation in diabetic rats", *J. Pharm. Pharmacol.*, 40:716–717 (1988).

Fong, J.W., "Microencapsulation by Solvent Evaporation and Organic Phase Separation Processes," pp. 81–108, chapter 5 from *Controlled Release Systems: Fabrication Technology*, Ed. Dean Hsieh, Ph.D., vol. 1 1998.

Masters, David B., et al., "Prolonged Regional Nerve Blockade by Controlled Release of Local Anesthesia from a Biodegradable Polymer Matrix", *Anesthesiology*, 79:340–346 (1993).

Fong, Jones W., et al., "Evaluation of biodegradable microspheres prepared by a solvent evaporation process using sodium oleate as emulsifier", *Journal of Controlled Release*, 3:119–130 (1986).

Berde, C.B., et al., "Sustained Release of Dibucaine from a Biodegradable Polymer Matrix: A Potential Method for Prolonged Neural Blockade", Abstracts of Scientific Papers, 1990 Annual Meeting, Amer. Soc. Anesthesiologists, 73:A776 (Sep. 1990).

Edelman, Elazer R., et al., "Optimization of release from magnetically controlled polymeric drug release devices", *Biomaterials*, 14(8):621–626 (1993).

Masters, et al., Abstract No. 94.3, "Prolonged Sciatic Nerve Blockade Using Sustained Release of Veratridine From a Biodegradable Polymer Matrix", *Soc. Neurosci. Abstr.*, 18:200 (1992).

* cited by examiner

PROLONGED ANESTHESIA IN JOINTS AND BODY SPACES

This application is a continuation of U.S. patent application Ser. No. 09/109,324, filed Jul. 2, 1998, now U.S. Pat. No. 6,248,345, which claims priority from U.S. Provisional Application Serial No. 60/051,601 filed Jul. 2, 1997.

FIELD OF THE INVENTION

The present invention is related to sustained release formulations for the administration of locally active agents and/or diagnostic agents in sustained release form intra articularly or in other body spaces. In particular embodiments, the invention provides methods and compositions for the administration of local anesthetics as well as compositions and methods for augmenting the duration and potency of local anesthesia, in patients in need thereof, and for obtaining additional beneficial effects, in intra articular locations and in all human or animal body spaces.

BACKGROUND OF THE INVENTION

Symptomatic treatment of joint pain has hereto been based on the use of systemic treatment with steroidal and nonsteroidal antiinflammatory agents and analgesics as well as localized injection of steroidal antiinflammatories, e.g., intra articular injection, and local anesthetics, either intra articular or proximal to the innervation of the painful joint. Localized treatment is generally preferred over systemic treatment, particularly when treating severe, localized joint pain, in order to avoid the untoward systemic effects associated with the high levels of both steroidal and nonsteroidal antiinflammatory agents otherwise required. Local anesthetics alone have previously been injected into joint spaces to relieve pain, with mixed results.

While compounds utilized as general anesthetics reduce pain by producing a loss of consciousness, local anesthetics act by producing a loss of sensation in the localized area of administration in the body. The mechanism by which local anesthetics induce their effect, while not having been determined definitively, is generally thought to be based upon the ability to interfere with the initiation and transmission of the nerve impulse. The duration of action of a local anesthetic is proportional to the time during which it is in actual contact with the nervous tissues. Consequently, procedures or formulations that maintain localization of the drug at the nerve greatly prolong anesthesia.

Local anesthetics are potentially toxic, yet must remain at the site long enough to allow sufficient time for the localized pain to subside. Therefore, it is of great importance that factors such as the choice of drug, concentration of drug, and rate and site of administration of drug be taken into consideration when contemplating their use.

Different devices and formulations are known in the art for administration of local anesthetics. For example, local anesthetics can be delivered in solution or suspension by means of injection, infusion, infiltration, irrigation, topically and the like. Injection or infusion can be carried out acutely, or if prolonged local effects are desired, localized anesthetic agents can be administered continuously by means of a gravity drip or infusion pump. Thus, local anesthetics such as bupivacaine have been administered by continuous infusion, e.g., for prolonged epidural or intrathecal administration.

Sustained release carriers for local anesthetics have been described. For example, U.S. Pat. Nos. 4,725,442 and 4,622,219 (Haynes) are directed to methoxyflurane-containing microdroplets coated with a phospholipid prepared by sonication, which are suitable for intradermal or intravenous injection into a patient for inducing local anesthesia. Such microdroplets are said to cause long-term local anesthesia when injected intradermally, giving a duration of anesthesia considerably longer than the longest acting conventional local anesthetic (bupivacaine).

U.S. Pat. No. 5,188,837 (Domb) relates to a microsuspension system containing liposphere having a layer of a phospholipid imbedded on their surface. The core of the liposphere is a solid substance to be delivered, or the substance to be delivered is dispersed in an inert vehicle. The substance to be delivered can be, e.g., nonsteroidal antiinflammatory compounds, local anesthetics, water insoluble chemotherapeutic agents and steroids.

Other formulations directed to injectable microcapsules, etc. are known. For example, U.S. Pat. No. 5,061,492 describes prolonged release microcapsules of a water-soluble drug in a biodegradable polymer matrix which is composed of a copolymer of glycolic acid and a lactic acid. The microcapsules are prepared as an injectable preparation in a pharmaceutically acceptable vehicle. The particles of water soluble drug are retained in a drug-retaining substance dispersed in a matrix of the lactic/glycolic acid copolymer in a ratio of 100/1 to 50/50 and an average molecular weight of 5,000–200,000. The injectable preparation is made by preparing a water-in-oil emulsion of an aqueous layer of drug and drug retaining substance and an oil layer of the polymer, thickening and then water-drying.

U.S. Pat. No. 4,938,763 (Dunn, et al.) is related to a biodegradable polymer for use in providing syringe able, in-situ forming, solid biodegradable implants for animals. In one aspect of this reference, a thermosetting system is utilized which utilizes copolymers which may be derived from polylactides and/or polyglycolides, combinations and mixtures of these and other polymers.

U.S. Pat. No. 4,293,539 (Ludwig, et al.) is directed to controlled release formulations comprised of a microbial agent dispersed throughout a copolymer derived from lactic acid and glycolic acid. The copolymer is derived from 60–95% lactic acid and 40-5% glycolic acid by weight, and has a molecular weight of 6,000–35,000. An effective amount of the copolymeric formulation is administered by subcutaneous or intramuscular administration.

WO 94/05265 describes improved biodegradable sustained release systems consisting of a polymeric matrix incorporating a local anesthetic for the prolonged administration of the local anesthetic agent. The devices are selected on the basis of their degradation profiles: release of the topical anesthetic in a linear, controlled manner over the period of preferably two weeks and degradation in vivo with a half-life of less than six months, more preferably two weeks, to avoid localized inflammation. The disclosure states that an anti-inflammatory can be incorporated into the polymer with the local anesthetic to reduce encapsulation for optimal access of drug to its site of action. The anti-inflammatories that are said to be useful include steroids such as dexamethasone, cortisone, prednisone, and others routinely administered orally or by injection.

Several non-glucocorticoids have been reported to prolong the action of local anesthetics. Epinephrine in immediate release form is known by those of ordinary skill in the art to briefly prolong the action of immediate release local anesthetics by inducing vasoconstriction adjacent to the site of injection. However, the duration of prolongation provided by immediate release epinephrine is on the order of about an hour, at best, in a highly vascularized tissue. This strategy is also severely limited by the risk of gangrene due to prolonged impairment of blood flow to local tissues. Dextrans and alkalinizing agents have also been suggested as local anesthesia prolonging agents, but have heretofore been reported to be ineffective for this purpose (Bonica et al., 1990, "Regional Analgesia With Local Anesthetics" THE MANAGEMENT OF PAIN, Second Edition, Volume II, Published, Lea & Febiger, Chapter 94, pages 1890–1892).

Colchicine has been shown to suppress injury-induced ectopic nerve discharge in a model system of chronic pain utilizing injured nerve (Wall et al.), 1995, Textbook of Pain, Third Edition, Publ., Churchill Livingston, pages 94–98; Devol et al., 1991, *A Group Report: Mechanisms of neuropathic pain following peripheral injury.* In: Basbaume A I, et al (eds). TOWARDS A NEW PHARMACOTHERAPY OF PAIN, Dahlem Konferenzen, Wiley, Chichester pp. 417–440; Devor et al., 1985, *Pain,* 22:127–137 at 128; and Devor, 1983, *Pain* 16:73–86). It has been reported in one study that colchicine was given for the treatment of low-back pain, although oral colchicine has been shown to be ineffective for the same indication (Schnebel et al., 1988, Spine 13(3):354–7). However, it has not heretofore been known to use colchicine to prolong local anesthesia.

A relatively long-acting local anesthetic, bupivacaine hydrochloride, is commercially available as Marcaine® Hydrochloride in sterile isotonic solutions with and without epinephrine (as bitartrate) 1:200,000 for injection via local infiltration, peripheral nerve block, and caudal and lumbar epidural blocks. After injection of Marcaine for caudal, epidural or peripheral nerve block in man, peak levels of bupivacaine in the blood are reached in 30 to 45 minutes, followed by a decline to insignificant levels during the next three to six hours.

In addition, polymer microparticles have long been used for both medical and non-medical applications where sustained release of an agent of interest is desired. Nevertheless, prior to the present invention, it would have been expected that polymer microparticles in a joint space would scratch the extremely smooth and slippery opposed intra articular surfaces or otherwise irritate or inflame the joint. Thus, the need for an effective method and formulation for delivering pain relief and other pharmaceutical or diagnostic treatments to the intra articular space has remained unmet until the present invention. Further, the need for an effective method and formulation for delivering pain relief and other pharmaceutical or diagnostic treatments to all body spaces has remained unmet until the present invention.

OBJECTS AND SUMMARY OF THE INVENTION

It is an object of the present invention to provide a biodegradable sustained release dosage form for providing prolonged administration of an active agent for the treatment and/or diagnosis of joint pain and/or other intra articular conditions in humans and animals. More particularly, it is an object of the invention to provide a local anesthetic in a biocompatible, biodegradable sustained release form in combination with an amount of an augmenting agent effective to enhance and prolong local anesthesia in joints and body spaces/cavities.

It is a further object of the present invention to provide a method for prolonging the effect of a local anesthetic agent in joints and/or body spaces/cavities and to further provide a prolonged and beneficial antiinflammatory effect.

It is a further object of the present invention to provide a biocompatible, biodegradable controlled release dosage form for providing prolonged local anesthetic treatment of body spaces in humans and animals, with or without other active agents described herein.

In accordance with the above-mentioned objects and others, the invention is related to formulations and methods for the localized and prolonged intra articular administration of active agents by the intra articular administration of a sustained release formulation according to the invention.

The sustained release formulation preferably comprises any agent suitable for the treatment or diagnosis of an intra articular condition.

The method according to the invention includes, for example, administering into an articular joint, a formulation of a biocompatible sustained release material and one or more active agents suitable for the purpose. The active agents can include one or more enzymes, anti-infectives, antibodies, and the like, diagnostic agents, as well as local anesthetics, local anesthesia augmenting agents and combinations thereof.

The active agents are preferably a local anesthetic and a non-toxic augmenting agent effective to potentiate or prolong the action of the local anesthetic effect. The sustained release material is in the form, e.g., of a plurality of microparticles including local anesthetic and said microparticles are suspended in a pharmaceutically acceptable vehicle for injection.

The formulation can include a local anesthetic augmenting agent, at least a portion of which is optionally incorporated in the sustained release material. In addition, at least a portion of the augmenting agent may optionally be in immediate release form.

In one aspect, the sustained release material comprises a polymer such as polyanhydrides, copolymers of acid and glycolic acid, poly(lactic) acid, poly(glycolic) acid, polyesters, polyorthoesters, proteins, polysaccharides and/or combinations thereof. Preferably, the polymers are biodegradable so that manual removal is avoided. Alternatively, the polymers are biocompatible and not biodegradable, in those circumstances wherein it is desirable to physically remove and/or wash out a local anesthetic formulation inserted into a joint space.

The sustained release formulation can contain any quantity of local anesthetic compatible with the selected polymer formulation. Preferably, the local anesthetic is incorporated into the sustained release material at a percent loading of 0.1% to 90% by weight. Any local anesthetic known to the art may be employed. Preferred local anesthetics include bupivacaine, ropivacaine, dibucaine, etidocaine, tetracaine, lidocaine, xylocaine, mixtures thereof, and/or salts and derivatives thereof.

Augmenting agents useful in potentiating pain relief and/or extending the duration of activity include, for example glucocorticosteroids, alphaxalone, allotetrahydrocortisone, aminopyrine, benzamil, clonidine, minoxidil, dehydroepiandrosterone, dextran, diazepam, diazoxide, ouabain, digoxin, spantide, taxol, tetraethylammonium, valproic acid, vincristine, a catecholamine in sustained release form, 1-[6-[[17-beta-3-methoxyestra-1,3,5(10)-triene-17-yl]amino]hexl]-1-H-pyrrole-2,5-dione, and active derivatives, analogs and mixtures thereof.

Useful glucocorticoid agents include, for example, dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone.

One skilled in the art will appreciate that an augmenting agent can be optionally included in the extended duration local anesthetic formulation in an amount compatible with, e.g., the extended release material and/or in an amount selected to enhance or prolong the duration of pain relief to the extent desired. For example, an augmenting agent, or combinations of augmenting agents, is incorporated into the formulation substrate at a percent loading ranging from about 0.001% to about 30% by weight, preferably from about 0.005% to about 15%, by weight.

The augmenting agent is preferably effective to prolong the duration of local anesthesia in a treated joint from about 15% to about 1400% of the duration of local anesthesia induced by sustained release local anesthetic without the augmenting agent.

Dextran augmenting agents may have any suitable molecular weight, but preferably have a molecular weight ranging from about 20 kDa to about 200 kDa and are optionally incorporated into said substrate at a percent loading ranging from about 0.01% to about 30% by weight.

In addition, an augmenting agent can include or comprise a vasoconstrictor agent in sustained release form. Preferred vasoconstrictor agents include, for example, clonidine, guanfacine, guanabenz, dopa, methyldopa, ephedrine, amphetamine, methamphetamine, methylphenidate, ethylnorepinephrine, ritalin, pemoline, epinephrine, norepinephrine, dopamine, metaraminol, phenylephrine, methoxamine, mephentermine, ephedrine, methysergide, ergotamine, ergotoxine, dihydroergotamine, sumatriptan and analogs, including active metabolites, derivatives and mixtures of any of the foregoing.

The invention also provides formulations effective to provide localized pain relief when administered into an intra articular space. The formulation includes, for example, a local anesthetic incorporated in a sustained release formulation, an effective amount of a biocompatible material, and an amount of an augmenting agent effective to prolong the duration of the local anesthesia.

Microparticles according to the invention that are suitable for deposit at a site in a patient in need of local anesthesia can optionally be prepared in lyophilized form, e.g., for rehydration prior to use.

The formulation, e.g., in the form of lyophilized particles is also desirably prepared in unit dosage form that is sterilized and provided in a container including an amount of such lyophilized particles sufficient to induce prolonged local anesthesia in at least one patient upon suspension in a solution acceptable for deposit into a patient.

Examples demonstrate prolongation of the duration of local anesthesia with the greater prolongation being provided by the combination of a local anesthetic with either a glucorticoid or a non-glucocorticoid augmenting agent.

Preferably, the formulation is in a form suitable for suspension in isotonic saline, physiological buffer or other solution acceptable for injection into a patient.

In certain preferred embodiments of the invention, the local anesthetic is prepared in matrices of biodegradable controlled release injectable microspheres. Optionally, the augmenting agent is incorporated into these matrices along with the local anesthetic.

In further embodiments, a suspension comprising a plurality of biocompatible, biodegradable controlled release microspheres comprising a local anesthetic agent, together with an augmenting agent is incorporated in the controlled release microspheres, or dissolved or suspended in the suspension of microspheres. The suspension is, for example, suitable for administering the microspheres by injection.

In yet additional embodiments of the present invention, the local anesthetic is incorporated into a controlled release matrix having the augmenting agent coated on the surface thereof.

In yet additional embodiments of the invention, the formulation comprises a local anesthetic core; an augmenting agent present in the core in an amount effective to prolong the effect of the local anesthetic in an environment of use, and a biocompatible, biodegradable coating on the core providing a slow release of the local anesthetic and/or augmenting agent in an environment of use.

In further embodiments, a portion or all of the local anesthetic is incorporated onto an outer surface of the coated substrate and a portion or all of the augmenting agent is optionally incorporated in the core, so that, e.g., augmenting agent continues to be released after the local anesthetic has dispersed from the controlled release material.

The augmenting agent may be systemically administered by injection or infiltration, instillation, oral dosing or other method to obtain the desired prolongation of effect. Systemic administration, (e.g., oral or intravenous) while effective, will require a higher total dose of an augmentation agent than with local administration in proximity to the local anesthetic.

The controlled release local anesthetic dosage form may be injected or infiltrated, with or without an augmenting agent, at the site where the anesthetic is to be released. This can be prior to surgery, at the time of surgery, or following removal (discontinuation) or reversal of a systemic anesthetic.

In one preferred embodiment, the formulation is prepared in the form of microspheres. The microspheres may be prepared as a homogenous matrix of a local anesthetic with a biodegradable controlled release material, with the augmenting agent optionally incorporated therein. The microspheres are preferably prepared in sizes suitable for infiltration and/or injection, and injected at the site where the anesthetic is to be released before surgery, during the time of surgery, or following removal or reversal of systemic anesthetic.

Examples of intra articular joints where the formulations useful in the invention can be administered include knee, elbow, hip, sternoclavicular, temporomandibular, carpal, tarsal, wrist, ankle, and any other joint subject to arthritic conditions; examples of bursae where the formulations useful in the invention can be administered include acromial, bicipitoradial, cubitoradial, deltoid, infrapatellar, ishchiadica, and other bursa known to those skilled in the art to be subject to pain.

The formulations of the invention are also suitable for administration in all body spaces/cavities, including but not limited to pleura, peritoneum, cranium, mediastinum, pericardium, bursae or bursal, epidural, intrathecal, intraocular, etc.

The invention is further directed to the use of a formulation comprising (a) controlled release microparticles comprising a local anesthetic and an effective amount of a biocompatible, biodegradable sustained release material prolonging the release of the local anesthetic from the formulation, and (b) a non-toxic augmenting agent in an amount effective to prolong the effect of the local anesthetic in-vivo, to treat localized joint pain or pain arising from a body space. Preferably, at least a portion of said augmenting agent is incorporated into said microparticles.

The microparticles are preferably suspended in a pharmaceutically acceptable vehicle for injection. The formulation may further comprise an active agent selected from the group consisting of an enzyme, an anti-infective agent, an antibody, a diagnostic aid, a radio-opaque dye, a magnetic resonance imaging dye, a radiolabeled agent, and combinations thereof. Preferably, at least a portion of said further active agent is incorporated into said microparticles. The local anesthetic is preferably incorporated into the microparticles at a percent loading of 0.1% to 90% by weight. In certain preferred embodiments, the local anesthetic is bupivacaine, the augmenting agent is dexamethasone, and the sustained release material is a poly(lactide co-glycolide). In further preferred embodiments, the microparticles comprise local anesthetic in a percent loading between 0.1% and 90%, preferably between 65 and 80%, and augmenting agent is a glucocorticosteroid agent present in a weight percent relative to the local anesthetic from 0.005% to 15%.

The invention further is directed to the use of a formulation comprising (a) controlled release microparticles comprising a local anesthetic and an effective amount of a biocompatible, biodegradable sustained release polymer selected from polyanhydrides, copolymers of lactic acid and glycolic acid, poly(lactic) acid, poly(glycolic) acid, polyesters, polyorthoesters, proteins, polysaccharides and combinations thereof, providing an in-vitro release of said local anesthetic of from 10 to 60 percent after 24 hours, from 20 to 80 percent release after 48 hours, and from 40 to 100 percent release after 72 hours; and (b) a non-toxic augmenting agent in an amount effective to prolong the effect of the local anesthetic in-vivo, for providing pain relief a body space selected from pleura, peritoneum, cranium, mediastinum, pericardium, bursae or bursal, epidural, intrathecal, and intraocular, or from intra articular joints selected from knee, elbow, hip, sternoclavicular, temporomandibular, carpal, tarsal, wrist, ankle, and any other joint subject to arthritic conditions, or from bursae selected from acromial, bicipitoradial, cubitoradial, deltoid, infrapatellar, ishchiadica, and other bursa known to those skilled in the art to be subject to pain, and which formulation when administered in-vivo for at least about 24 hours, and preferably for 3–5 days. The formulation may in certain embodiments preferably comprise a second active agent selected from an enzyme, an anti-infective agent, an antibody, a diagnostic aid, a radio-opaque dye, a magnetic resonance imaging dye, a radiolabeled agent, and combinations thereof.

DETAILED DESCRIPTION

Figure 1:
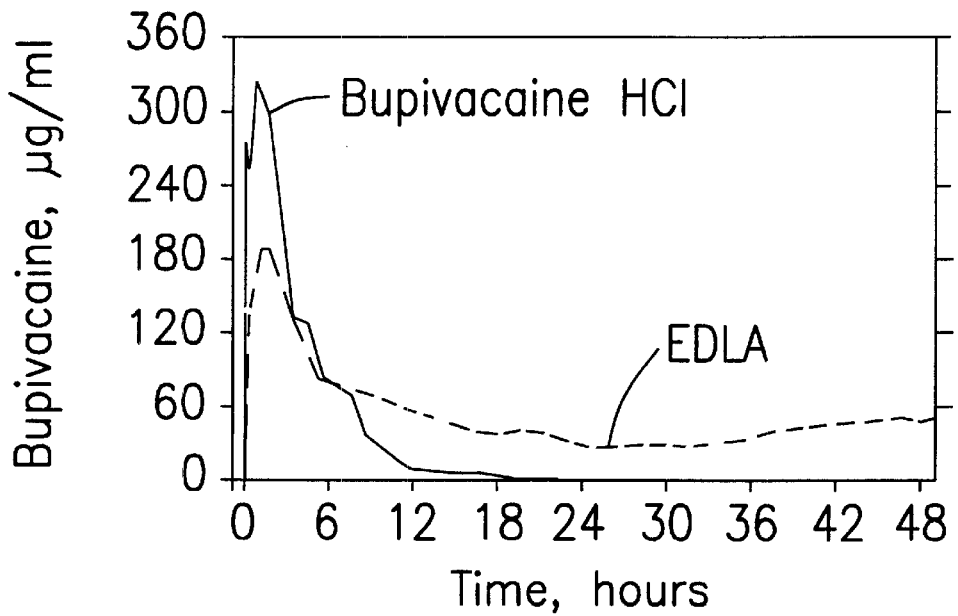
FIG. 1 charts for n=2 test animal, the local concentrations verses time, in hours, of bupivacaine concentrations at an intramuscular site of an injection of extended duration local anesthetic ("EDLA"), in the form of bupivacaine-containing microspheres. The local concentrations are determined by microdialiysis conducted at the site of injection and calibrated by a perfusion of a known bupivacaine concentration. The dotted curve shows local concentrations following release of bupivacaine from EDLA and the solid curve shows local concentrations following injection of bupivacaine HCl (1 mg) in immediate release form.

Accordingly, in a surprising and unexpected finding, methods are provided for the administration of microparticles in a form suitable for injection and containing one or more active agents suitable for treating and/or diagnosing a disease or painful condition in one or more articular joints in a patient in need thereof. Thus, the invention provides a safe and effective procedure for the intra articular administration of such active agents in sustained release form without causing damage, irritation or inflammation to the treated tissue. Prior to the invention, it was believed that the microparticles might cause injury and thus be intolerable intra articularly. However, as demonstrated herein, the microparticles were adequately tolerated. In further embodiments, the microparticles are administered into a body space or cavity.

Thus, the present invention provides formulations and methods for the safe and effective treatment of localized joint conditions by the administration, e.g., by injection, infusion or infiltration of extended duration local anesthetic microparticles into an intra articular space and/or body space in need of such treatment.

In a preferred aspect, the invention provides methods for relieving localized joint pain and/or inflammation. In this aspect of the invention, the formulations according to the invention include an effective amount of a local anesthetic agent and preferably an amount of an augmenting agent, e.g., a glucocorticosteroid or nonglucocorticoid agent that may be provided in any form suitable for intra articular placement, including forms molded for insertion into a joint space, pastes, solutions and the like. The augmentation of efficacy provided by the use of the augmenting agent cannot be predicted based on in-vitro release (dissolution) of the local anesthetic in sustained release form. The inclusion of the augmenting agent within the sustained release formulations of the invention does not substantially alter or prolong the in-vitro dissolution rate of the local anesthetic agent from the formulation; yet, the same formulation when administered in-vivo provides a rapid onset of local anesthesia and a significant increase in the time period of local anesthesia at the site of administration. The augmenting agents disclosed herein are both glucocorticoid and nonglucocorticoid agents and can be administered prior to, along with, or after administration, e.g., topical application, infiltration and/or injection of the local anesthetic agent in sustained release form, in each case with a substantial prolongation of local anesthesia in-vivo.

The augmenting agent can be compounded in the same sustained release formulation as a local anesthetic agent or agents, in a separate sustained release formulation, e.g., different injectable microspheres, or in a non-sustained release, i.e, immediate release formulation. The augmenting agent may be administered before, simultaneously with, or after injection or infiltration, implantation or insertion of the sustained release local anesthetic formulation at the desired site.

In those embodiments of the invention directed to formulations where the augmenting agent is included in the formulation with the local anesthetic, the augmenting agent may be included in sustained release form or in immediate release form. The augmenting agent may be incorporated into any pharmaceutically acceptable carrier and preferably a carrier providing sustained release, including, e.g., a sustained release matrix along with the local anesthetic; incorporated into a sustained release coating on a sustained release device or formulation; or incorporated as an immediate release layer coating the local anesthetic formulation. On the other hand, the augmenting agent may be incorporated into a pharmaceutically acceptable aqueous medium suitable for infiltration or injection, either in sustained release form or in immediate release form.

The sustained release formulations and methods of the invention may be used in conjunction with any system for application, infiltration, implantation, insertion, or injection known in the art, including but not limited to microparticles, e.g., microspheres or microcapsules, gels, pastes, and the like.

As used herein, the terms, "sustained release" and "controlled release" indicate a prolongation of the duration of release and/or duration of action of an active agent and are well understood in the art and are intended to be interchangeable, unless otherwise indicated.

As used herein, the term, "active agent" includes, without limitation, any substance that it is desired to incorporate into microparticles for sustained or controlled intra articular delivery and/or release. An active agent can be either soluble or insoluble in a polymer solvent and may be in any state, including liquids, solutions, pastes, solids, and the like. The active agent may be a pharmaceutically active agent, such as a drug and/or diagnostic substance for human or veterinary use. An active agent can also be an enzyme, antibody, antigen or other biological protein or peptide for pharmaceutical and/or diagnostic use or combinations thereof. An active agent may also be, simply by way of example, any art known agent, e.g., a polypeptide or peptide derivative effective to protect or regenerate cartilage and/or connective tissue.

Additional pharmaceutically active agents that can be incorporated into microparticles for intra articular administration, include, e.g., antibiotics such as sulfisoxazole, penicillin G, ampicillin, cephalosporins, amikacin, gentamicin, tetracyclines, chloramphenicol, erythromycin, clindamycin, isoniazid, rifampin, and derivatives, salts and mixtures thereof; antifungals such as amphotericin B, nystatin, ketoconazole; antivirals such as acyclovir, amantadine; anticancer agents such as cyclophosphamide, methotrexate, etretinate and other art known anti-infective or antitumor agents or combinations thereof.

Diagnostic agent that can be administered intra articularly according to the invention include, e.g., dyes, vital dyes, radio-opaque dyes, magnetic resonance imaging dyes, electron spin dyes, radio-isotope labeled moieties and others readily apparent to the artisan, or combinations thereof. In a preferred embodiment, the formulation can be prepared, e.g., to include any art-known nontoxic and radio-opaque dye, e.g., an iodine compound and the like, to aid in the visualization of the site for improved accuracy of administration and where desirable, to monitor the location of any controlled release material remaining at the site at a later time. In another embodiment, at least a portion of such optional radio-opaque dye is present in the suspending vehicle to assist in the localization of the site of injection.

Prodrugs are well known in the art and include inactive drug precursors which, when exposed to high temperature, metabolizing enzymes, cavitation and/or pressure, in the presence of oxygen or otherwise, or when released from the microspheres, will form active drugs in the intercellular or intracellular environment. Suitable prodrugs will be apparent to those skilled in the art.

Examples of antibodies that can be incorporated into microparticles by this method generally include industrial antibodies as well as antibodies and derivatives of antibodies for use in biotechnological process as well as antibodies for diagnostic and therapeutic purposes. Such antibodies include, for example, IgA, IgD, IgG, IgE IgM, and combinations thereof, in the form of monoclonal, polyclonal and recombinant antibodies, catalytic antibodies and antigen-binding antibodies. Further, fragments of antibodies can be incorporated, together with or separately from, intact antibodies. For example, antibody fragments include light and/or heavy chains, and combinations of light chains or heavy chains, as well as the Fab, Fv, Fc, Fd and smaller fragments, such as active portions of the variable region and non-naturally occurring combinations of such fragments and/or light and heavy chains or combinations thereof. Recombinant polypeptides with antibody activity can also be incorporated into microparticles by this method, as can engineered antibodies or antibodies or antibody fragments that are linked to other molecules, e.g., drugs, prodrugs and/or diagnostic or analytic label moieties or combinations thereof.

Examples of genetic materials that can be incorporated, include, e.g., nucleic acids such as RNA and DNA, of either natural or synthetic origin, including recombinant RNA and DNA and antisense RNA and DNA as well as chemical derivatives of these nucleic acids, e.g., phosphonamides. Types of genetic material that may be incorporated include, for example, genes carried on expression vectors such as plasmids, phagemids, cosmids, yeast artificial chromosomes (YACs), and defective or "helper" viruses, anti-gene nucleic acids, both single and double stranded RNA as well as viral vectors for transforming cells, in vivo or in vitro or for genetic therapy, e.g., retroviral vectors, adenoviral vectors and the like or combinations thereof.

Examples of enzymes that can be incorporated into microparticles by this method include, generally, enzymes for diagnosis and therapeutic purposes, e.g., ribonuclease, neuramidinase, trypsin, glycogen phosphorylase, amino peptidase, trypsin chymotrypsin, amylase, muramidase, diesterase, glutamic acid dehydrogenase, as well as fibrinolytic enzymes, lysozymes, dextranase and ribozymes or combinations thereof, to name but a few that will be readily apparent to the artisan.

As used herein, the terms "local anesthetic agent" or "local anesthetic" means any drug which provides local numbness and/or analgesia. The term also includes, but is not limited to, any drug which, when locally administered, e.g, topically or by infiltration or injection, provides localized full or partial inhibition of sensory perception and/or motor function. Under either definition, the localized condition so induced is also referred to herein as "local anesthesia". Local anesthesia can result, for example, from contact of an effective amount of a local anesthetic with sensory nerve processes at the site at which the painful stimulus is present, or can result from inhibition of nerve transmission at a nerve or nerves proximal to the site at which the painful stimulus is present.

Local anesthetic agents which can be used include, simply by way of example, bupivacaine, ropivacaine, dibucaine, procaine, chloroprocaine, prilocaine, mepivacaine, etidocaine, tetracaine, lidocaine, and xylocaine, as well as anesthetically active derivatives, analogs and mixtures thereof. The local anesthetic can be in the form of a salt, for example, the hydrochloride, bromide, acetate, citrate, carbonate or sulfate.

More preferably, the local anesthetic agent is in the form of a free base. The free base provides a slower initial release and avoids an early "dumping" of the local anesthetic at the injection site. Preferred local anesthetic agents include, e.g., bupivacaine. Local anesthetic agents typically administered systematically may also be used in those cases where the means of administration results only in a local effect, rather than systemic.

The term "local anesthetic" may also encompass, pursuant to the definitions provided herein, a drug of a different class than those traditionally associated with local anesthetic properties, including but not limited to morphine, fentanyl, and agents which, for example, can provide regional blockage or localized anesthesia of nociceptive pathways (afferent and/or efferent).

As used herein, the term "microparticles" includes microspheres and microcapsules in a size range suitable for injection into a desired site of administration by injection, infiltration, infusion and the like. For administration by injection and/or infiltration or infusion, the formulations according to the invention may be suspended (e.g., for microparticles), or dissolved (e.g., for immediate release forms), in any art-known vehicle suitable for injection and/or infiltration or infusion. Such vehicles include, simply by way of example, isotonic saline, buffered or unbuffered and the like and may optionally include any other art known ingredients or agents, e.g., colorants, preservatives, antibiotics, epinephrine and other art known ingredients. A more complete listing of art-known vehicles for administration of formulations by systemic administration and/or local injection and/or infiltration is provided by reference texts that are standard in the art, for example, *REMINGTON'S PHARMACEUTICAL SCIENCES*, 16th Edition, 1980 and 17th Edition, 1985, both published by Mack Publishing Company, Easton, Pa., the disclosures of which are incorporated by reference herein in their entireties.

Formulations according to the invention provide extended duration local anesthetic and may be referred to hereinbelow as "EDLA" formulations.

As used herein, the term "patient" broadly refers to any animal that is to be treated with the compositions and by the methods herein disclosed. The disclosed extended duration micropartical formulations and methods for intra articular administration can provide prolonged and effective administration of active agents. In particular, the method for intra articular administration of extended duration local anesthetic dosage forms according to the invention can provide localized pain blockade to any animal, e.g., any vertebrate, which it is desired to so anesthetize. In particular, the disclosed methods and compositions will find use in veterinary practice and animal husbandry for, e.g., birds and mammals, wherever prolonged local anesthesia is convenient or desirable. In a preferred embodiment, the term "patient" includes humans in need of or desiring prolonged intra articular treatments, such as for treatment of joint pain.

Augmenting Agents

Augmenting agents according to the invention are compositions or compounds that prolong the duration of local anesthesia and/or enhance the effectiveness of local anesthetic agents when delivered to the site of local anesthetic administration before, simultaneously with or after the local anesthetic is administered.

In certain embodiments of the invention, the augmenting agent can be from one or more of the following general types or classes of agents, including glucocorticosteroid agents, alkalinizing agents, non-glucocorticoid steroids such as, e.g, neuroactive steroids and/or steroid or nonsteroid modulators of gamma amino butyric acid ("GABA") receptors, modulators of ionic transport across cell membranes, including, e.g., modulators of membrane transport of monovalent and divalent metal ions such as, for example, blockers or enhancers of sodium, potassium and/or calcium transport across cell membranes, antipyretic agents, adrenergic receptor agonists or antagonists, such as $\alpha 2$ receptor agonists, tubulin binding agents, including, e.g., agents that are capable of either causing formation or disruption of intracellular microtubules, osmotic polysaccharides, agonists and antagonists of potassium ATP channels, i.e., able to open or close potassium ATP channels, Na, K-ATPase inhibitors and enhancers, neurokinin antagonists, PLC (i.e., phosphatidylinositol-specific phospholipase C) inhibitors, inhibitors of leukocyte glucose metabolism and anti-convulsants. The augmenting agent can also be an analeptic, a tranquilizing agent, an ataretic, an antidepressant, an anti-seizure agent, leukotriene and prostaglandin agonists and inhibitors, phosphodiesterase agonists and inhibitors, e.g., based on cAMP, and combinations of any of the foregoing. Vasoconstrictive agents provided in controlled release form also provide for unexpected and surprising augmentation of duration and potency of local anesthetics relative to immediate release forms of vasonstrictive agents heretofore known to the art. The aforementioned types of augmenting agents may to used alone or in any mixture or combination of each such agent to provide effective augmentation of local anesthesia where desired.

In one embodiment, the augmenting agent is any art-known glucocorticosteroid agent, such as, simply by way of example, dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone, ropivicaine and pharmaceutically acceptable mixtures and salts thereof and any other derivatives and analogs thereof.

When a glucocorticosteroid agent is included in the controlled release substrates comprising local anesthetic, it has been found that useful loadings of glucocorticosteroid agent are, e.g., from 0.005% to 30% by weight of the substrate.

When the glucocorticosteroid agent is included with a suitable vehicle in which microparticles comprising local anesthetic are suspended, the glucocorticosteroid agent is present, for example, in a weight percent relative to the local anesthetic varying from about 0.005% to about 15%.

In another embodiment, the augmenting agents include an alkalinizing agent. The alkalinizing augmenting agents used herein preferably raise the pH of the medium in which the local anesthetic agents in sustained release form are present (e.g., either an injection medium or the environment at the site of injection) to provide a pH from about 6.0 to about 8.5, preferably from about 7.5 to about 8.5. Preferably, the alkalinizing agent may be, for example, a carbonate buffer such as sodium carbonate. Of course, any other alkalinizing agent that is pharmaceutically acceptable for localized injection or infiltration may also be effectively employed. The augmenting agents also include non-glucocorticoid steroids such as e.g., androgens, such as testosterone and its active derivatives, analogs and metabolites; estrogens, such as estradiol and its active derivatives, analogs and metabolites and progestins, such as progesterone and its active derivatives, analogs and metabolites and mixtures of any of these.

In yet another embodiment, the augmenting agents are neuroactive steroids, such as, e.g., one or more of the class of anesthetic steroids. Neuroactive steroids useful as augmenting agents according to the invention also include those which modulate GABA receptors. Preferred neuroactive steroids include, simply by way of example, althesin and its main component, alphaxalone and active analogs, derivatives and mixtures thereof, as well as 5-alpha-pregnane-3 alpha-21-diol-20-one (tetrahydrodeoxycorticosterone or THDOC) and/or allotetrahydrocortisone (the 17-beta configuration); and dehydroepiandrosterone ("DHE") and active analogs, derivatives and mixtures thereof. Preferably, the neuroactive steroids are present as an additive in the vehicle carrying the microspheres in a concentration ranging from about 0.01% to about 1% by weight, and most preferably from about 0.05% to about 0.5% by weight.

The augmenting agents also include non-steroidal modulators of GABA receptors, including those that are capable of potentiating the inhibitory effects of GABA on those receptors. Preferably, these include the benzodiazepines, e.g., diazepam as well as its active derivatives, analogs and metabolites and mixtures thereof. More preferably, the diazepam is present as an additive in the vehicle in a concentration ranging from about 0.01% to about 1% by weight, and most preferably from about 0.05% to about 0.5% by weight. Of course, the artisan will appreciate that the potency of benzodiazepines varies widely, and will adjust these concentration ranges accordingly for other benzodiazepines, relative to the potency of diazepam.

In yet another aspect of the invention, the augmenting agent is a modulator of ionic transport across cell membranes. Monovalent and multivalent metal ion transport can be modulated. Agents include, e.g., sodium, potassium and calcium channel modulators (e.g., nifedipine, nitrendipine, verapamil, etc.). In preferred embodiments, these also include, but are not limited to, aminopyridine, benzamil, diazoxide, 5,5 diphenylhydantoin, minoxidil, tetrethylammonium and valproic acid. Preferably, the ion transport modulating agent is present as an additive in the vehicle carrying the microspheres in a concentration ranging from about 0.01 to about 5 percent by weight, and most preferably from about 0.05 to about 1.5 percent by weight.

Augmenting agents also include, e.g., antipyretic agents such as aminopyrine, phenazone, dipyrone, apazone, phenylbutazone and derivatives and analogs thereof. Aminopyrine is preferably included in the vehicle containing the microspheres in a concentration ranging from about 0.01 to about 0.5 percent and in a more preferred embodiment the concentration ranges from about 0.05 to about 0.5 percent, by weight.

Other preferred augmenting agents include, e.g., adrenergic receptor modulators, such as α2 receptor agonists, can also be used as augmenting agents. Simply by way of example, the α2 receptor agonist clonidine provides useful augmentation of local anesthesia, although any other art known α2 receptor modulators capable of augmenting local anesthesia according to the invention may be used. Clonidine is preferably included in the vehicle containing the microspheres in a concentration ranging from about 0.01% to about 0.5% preferred embodiment the concentration ranges from about 0.05% to about 1%, by weight.

Tubulin binding agents that are capable of promoting the formation or disruption of cytoplasmic microtubules may be employed as augmenting agents according to the invention. Such agents include, for example, colchicine and the vinca alkaloids (vincristine and vinblastine) as well as active derivatives, analogs metabolites and mixtures thereof. Of course, some agents may be classified in more than one category, thus, for example, colchicine is also known to inhibit glucose metabolism in leukocytes. Colchicine is preferably included in the vehicle containing the microspheres in a concentration ranging from about 0.01 to about 1.0 percent and in a more preferred embodiment the concentration ranges from about 0.05 to about 0.5 percent, by weight.

Osmotic polysaccharides are also able to be used as augmenting agents. In one preferred embodiment, the osmotic polysaccharide includes dextran. More preferably, the dextran augmenting agents according to the invention have a molecular weight ranging from about 20 kDa through about 200 kDa, or greater. A solution containing dextran in a form suitable for injection or infiltration into a desired site in a patient is preferably buffered to a pH ranging from about 3.0 to about 8.5, but in a preferred aspect is buffered to a pH ranging from about 7.0 to about 8.5.

Other preferred embodiments of the invention provide for potassium-ATP channel agonists for use as augmenting agents. A preferred potassium-ATP channel agonist is, e.g., diazoxide, as well as its active derivatives, analogs, metabolites and mixtures thereof which are useful as augmenting agents.

Sodium/potassium ATPase inhibitors are also preferred as augmenting agents according to the invention. Preferably, the sodium/potassium ATPase inhibitors are cardiac glycosides that are effective to augment local anesthesia. Cardiac glycosides that are useful according to the invention include, e.g., oubaine, digoxin, digitoxin and active derivatives, analogs and metabolites and mixtures of any of these.

Additionally, augmenting agents according to the invention include, e.g., neurokinin antagonists, such as, e.g., spantide and other peptide inhibitors of substance P receptors that are well known to the art, e.g., as are listed in Receptor and Ion Channel Nomenclature Supplement, *Trends in Pharmacological Sciences* 18:64–65, the disclosure of which is incorporated by reference herein in its entirety. PLC (i.e., phosphatidylinositol-specific phospholipase C) inhibitors such as, e.g., 1-[6-[[17-beta-3-methoxyestra-1,3,5(10)-triene- 17-yl]amino]hexl]-1-H-pyrrole-2,5-dione, and anti-seizure agents and agents that stabilize cell membrane potential, such as, e.g., benzodiazepines, barbiturates, deoxybarbiturates, carbamazepine, succinamides, valproic acid, oxazalidienbiones, phenacemide and active derivatives, analogs and metabolites and mixtures thereof. Preferably, the anti-seizure augmenting agent is phenytoin, and most preferably is 5,5-diphenylhydantoin.

Surprisingly, locally acting vasoconstrictive agents also provide effective augmentation of local anesthesia that is unexpectedly superior to that provided by immediate release vasoconstrictive agents. While not wishing to be bound by any hypothesis as to how vasoconstrictive agents in sustained release form might greatly prolong local anesthetic activity, it is believed that sustained release vasoconstrictor agents provide a controlled and non-toxic vasoconstrictor activity that reduces the rate of local anesthetic washout from the treated tissue area to prolong the presence of effective concentrations of local anesthetic in the tissue. It is known to the art that vasoconstrictors, e.g., epinephrine, prolong local anesthetic activity for, at best, about 1 hour and that if excessive amounts of epinephrine or other vasoconstrictor is administered in an attempt to further prolong local anesthesia, local circulation may be so disrupted as to cause tissue necrosis and gangrene.

It is therefore unexpected that sustained release vasoconstrictor agents can achieve local tissue concentrations that are safe and effective to provide vasoconstrictor activity effective to substantially prolong local anesthesia. More unexpectedly, the local circulatory bed, i.e., blood vessels, remain responsive to the vasoconstrictor agent for prolonged periods, e.g., receptor desensitization or smooth muscle fatigue or tolerance does not prevent the prolongation effect. The gradual release from a sustained release formulation also serves to greatly reduce the risk of toxic reactions such as, e.g., localized tissue necroses.

The previously discussed vasoconstrictive augmenting agents can be administered before, simultaneously with or after the administration of local anesthetic. In one embodiment of the invention, at least a portion of the vasoconstrictive agent is formulated in a sustained release formulation together with local anesthetic. In another embodiment, the vasconstrictive agent is prepared in one or separate sustained release formulations. It will be appreciated that by manipulating the loading of, e.g., microspheres containing vasoconstrictor agent, the artisan can determine the number of microspheres necessary to administer a given dose. Thus, simply by way of example, microspheres loaded with about 75 percent by weight of vasoconstrictor agent will require half of the microspheres necessary to administer a predetermined dose than will microspheres loaded with about 45 percent by weight of vasoconstrictor agent.

Vasoconstrictor agents can formulated into, e.g., sustained release microspheres including both a local anesthetic, e.g., bupivacaine free base, and a vasoconstrictor agent. Vasoconstrictor agents can also be formulated into, e.g., sustained release microspheres including local anesthetic without a vasoconstrictive agent.

While not wishing to be bound by any hypothesis as to how vasconstrictive agents in sustained release form might greatly prolong local anesthetic activity, it is believed that sustained release vasoconstrictor agents provide a controlled and non-toxic vasoconstrictor activity that reduces the rate of local anesthetic washout from the treated tissue area to prolong the presence of effective concentrations of local anesthetic in the tissue. It is known to the art that vasoconstrictors, e.g., epinephrine, prolong local anesthetic activity for, at best, about 1 hour and that if excessive amounts of epinephrine or other vasoconstrictor is administered in an attempt to further prolong local anesthesia, local circulation may be so disrupted as to cause tissue necrosis and gangrene.

It is therefore unexpected that sustained release vasoconstrictor agents can achieve local tissue concentrations that are safe and effective to provide vasoconstrictor activity effective to substantially prolong local anesthesia. More unexpectedly, the local circulatory bed, i.e., blood vessels, remain responsive to the vasoconstrictor agent for prolonged periods, e.g., receptor desensitization or smooth muscle fatigue or tolerance does not prevent the prolongation effect. The gradual release from a sustained release formulation also serves to greatly reduce the risk of toxic reactions such as, e.g., localized tissue necroses.

Vasoconstrictor agents can formulated into, e.g., sustained release microspheres including both a local anesthetic, e.g., bupivacaine free base, and a vasoconstrictor agent. Vasoconstrictor agents can also be formulated into, e.g., sustained release microspheres including local anesthetic without a vasoconstrictive agent.

In one embodiment, local anesthetic and vasoconstrictor agents are administered simultaneously in the form of, e.g., separate microspheres suspended in a single medium suitable for injection or infiltration, or in separate microspheres suitable for injection, e.g., at the same site. In a further embodiment, simply by way of example, administration of sustained release microspheres with combined local anesthetic and vasoconstrictor agent can also be followed by one or more additional administrations of such combination formulation and/or of microspheres including as the active agent only local anesthetic or only vasoconstrictor agent.

Augmenting agents that are vasoconstrictor agents in sustained release form include, but are not limited to, catecholamines e.g., epinephrine, norepinephrine and dopamine as well as, e.g., metaraminol, phenylephrine, methoxamine, mephentermine, methysergide, ergotamine, ergotoxine, dihydroergotamine, sumatriptan and analogs, and alpha-1 and alpha-2 adrenergic agonists, such as, e.g., clonidine, guanfacine, guanabenz and dopa (i.e., dihyrdoxyphenylalanine), methyldopa, ephedrine, amphetamine, methamplietamine, methylphenidate, ethyl-norepinephrine ritalin, pemoline and other sympathomimetic agents, including active metabolites, derivatives and mixtures of any of the foregoing.

In a more preferred embodiment, at least a portion of any of the augmenting agents enumerated above are included in the sustained release formulation, in combination with a local anesthetic agent or agents in a concentration ranging from about 0.01 to about 30 percent or more, by weight, relative to the weight of the formulation.

The artisan will also appreciate that other augmenting agents according to the invention broadly include any other types and classifications of drugs or active agents known to the art. Such augmenting agents are readily identified by routine screening as discussed hereinbelow using animal sensory and motor quantitation protocols well known to the art.

A local anesthetic according to the invention can also be formulated, e.g., in injectable microspheres, in combination with at least one vasoconstrictor augmenting agent according to the invention. In one embodiment, the vasoconstrictor can be included in the vehicle suitable for injection carrying the microspheres. In a further embodiment, at least a portion of the vasoconstrictor can also be formulated into a sustained release formulation, e.g., injectable microspheres, together with the local anesthetic. In a still further embodiment, at least a portion of the vasoconstrictor can be prepared in a separate sustained release formulation.

The vasoconstrictor can be included in either a single or combination formulation in an amount ranging from about 0.001 percent to about 90 percent, by weight relative to the total weight of the formulation. Preferably, the vasoconstrictor is included in a sustained release formulation in an amount ranging from about 0.005 percent to about 20%, and more preferably, from about 0.05 percent to about 5 percent, by weight, relative to the total weight of the formulation. When a vasoconstrictor is present in the injection vehicle in immediate release form, it is present in amounts ranging from about 0.01% to about 5 percent, or more, by weight, relative to the injection vehicle. The vasoconstrictor can also be provided in a ratio of local anesthetic, e.g., bupivacaine to vasoconstrictor, ranging from about 10:1 to about 20,000 and preferably from about 100:1 to about 2000:1 and from about 500:1 to about 1500:1.

Of course, the artisan will appreciate that the amounts of augmenting agent and local anesthetic will vary depending upon the relative potency of the agents selected, the depth and duration of local anesthesia desired.

Of course, the artisan will appreciate that the optimal concentration and/or quantities or amounts of any particular augmenting agent, whether present in the injection vehicle, separately administered before, during or after local anesthesia is induced or whether included in the microsphere formulation, may be adjusted to accommodate variations in the treatment parameters. Such treatment parameters include the polymer composition of a particular microsphere preparation, the particular local anesthetic utilized, and the clinical use to which the preparation is put, in terms of the site treated for local anesthesia, the type of patient, e.g., human or non-human, adult or child, and the type of sensory stimulus to be anesthetized.

Further, the concentration and/or amount of any particular augmenting agent for a given formulation may be readily identified by routine screening in animals, e.g, rats, by screening a range of concentration and/or amounts of augmenting agent using the hotplate foot withdrawal assay and/or motor function assay described hereinbelow.

Art known methods are also available to assay local tissue concentrations, diffusion rates from microspheres and local blood flow before and after administration of local anesthetic formulations according to the invention. One such method is microdialysis, as reviewed by T. E. Robinson et al., 1991, *MICRODIALYSIS IN THE NEUROSCIENCES*, Techniques, volume 7, Chapter 1, pages 1–64, incorporated herein by reference in its entirety.

The methods reviewed by Robinson can be applied, in brief, as follows. A microdialysis loop is placed in situ in a test animal. Dialysis fluid is pumped through the loop. When microspheres according to the invention are injected adjacent to the loop, released drugs, e.g., bupivacaine and vasoconstrictor augmenting agents, are collected in the dialysate in proportion to their local tissue concentrations. The progress of diffusion of the active agents can be determined thereby with suitable calibration procedures using known concentrations of active agents. For the vasoconstrictor augmenting agents, decrements and durations of vasoconstriction effects can be measured by clearance rates of marker substances, e.g., methylene blue or radiolabeled albumen from the local tissue.

The data presented hereinbelow by the Examples applies microdialysis to confirm that bupivacaine containing microspheres placed into tissue provides an initial rise of free bupivacaine, followed by the prolonged maintenance of high local concentration.

The optimal concentration of augmenting agent for human clinical use may also be readily determined by routine animal screening as described hereinbelow, and further adjusted, where indicated, by routine clinical experience.

Formulations

Any pharmaceutically acceptable vehicle or formulation suitable for local infiltration or injection into a site to be anesthetized, that is able to provide a sustained release of an active agent may be employed to provide for prolonged local anesthesia as needed. Slow release formulations known in the art include specially coated pellets, polymer formulations or matrices for surgical insertion or as sustained release microparticles, e.g., microspheres or microcapsules, for implantation, insertion or injection, wherein the slow release of the active medicament is brought about through sustained or controlled diffusion out of the matrix and/or selective breakdown of the coating of the preparation or selective breakdown of a polymer matrix. Other formulations or vehicles for sustained or immediate delivery of an agent to a preferred localized site in a patient include, e.g., suspensions, emulsions, liposomes and any other suitable, art known, delivery vehicle or formulation.

In a preferred embodiment, the slow release formulation is prepared as microspheres in a size distribution range suitable for local infiltration or injection. The diameter and shape of the microspheres or other particles can be manipulated to modify the release characteristics. For example, larger diameter microspheres will typically provide slower rates of release and reduced tissue penetration and smaller diameters of microspheres will produce the opposite effects, relative to microspheres of different mean diameter but of the same composition. In addition, other particle shapes, such as, for example, cylindrical shapes, can also modify release rates by virtue of the increased ratio of surface area to mass inherent to such alternative geometrical shapes, relative to a spherical shape. The diameter of injectable microspheres are in a size range, for example, from about 5 microns to about 200 microns in diameter. In a more preferred embodiment, the microspheres range in diameter from about 20 to about 120 microns.

A wide variety of biocompatible materials may be utilized to provide the controlled/sustained release of the local anesthetic. Any pharmaceutically acceptable biocompatible polymers known to those skilled in the art may be utilized. It is preferred that the biocompatible sustained release material degrade in-vivo over a period of less than about two years, with at least 50% of the sustained release material degrading within about one year, and more preferably six months or less. More preferably, the sustained release material will degrade significantly within one to three months, with at least 50% of the material degrading into non-toxic residues which are removed by the body, and 100% of the drug being released within a time period from about two weeks to about two months. A degradable sustained release material should preferably degrade by hydrolysis, and most preferably by surface erosion, rather than by bulk erosion, so that release is not only sustained but also provides desirable release rates. However, the pharmacokinetic release profile of these formulations may be first order, zero order, bi- or multi-phasic, to provide the desired reversible local anesthetic effect over the desired time period.

In the case of polymeric materials, biocompatibility is enhanced by recrystallization of either the monomers forming the polymer and/or the polymer using standard techniques.

Suitable biocompatible polymers can be utilized as the sustained release material. The polymeric material may comprise biocompatible, biodegradable polymers such as a polylactide, a polyglycolide, a poly(lactide-co-glycolide), a polyanhydride, a polyorthoester, polycaprolactones, polyphosphazenes, polysaccharides, proteinaceous polymers, soluble derivatives of polysaccharides, soluble derivatives of proteinaceous polymers, polypeptides, polyesters, and polyorthoesters or mixtures or blends of any of these. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like. Preferred sustained release materials which are useful in the formulations of the invention include the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other useful polymers include protein polymers such as gelatin and fibrin and polysaccharides such as hyaluronic acid. Since polylactic acid takes at least one year to degrade in-vivo, this polymer should be utilized by itself only in circumstances where such a degradation rate is desirable or acceptable.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539 (Ludwig, et al.), the disclosure of which is hereby incorporated by reference in its entirety. In brief, Ludwig prepares such copolymers by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction may be conducted without solvents at a temperature from about 100° C. to about 250° C. for about 48 to about 96 hours, preferably under a reduced pressure to facilitate removal of water and by-products. The copolymer is then recovered by filtering the molten reaction mixture to remove substantially all of the catalyst, or by cooling and then dissolving the reaction mixture in an organic solvent such as dichloromethane or acetone and then filtering to remove the catalyst.

Various commercially available poly (lactide-co-glycolide) materials (PLGA) may be used in the preparation of the microspheres of the present invention. For example, poly(d,l-lactic-co-glycolic acid) are commercially available from Medisorb Technologies International L.P. (Cincinnati, Ohio). A preferred product commercially available from Medisorb is a 50:50 poly (D,L) lactic co-glycolic acid known as MEDISORB 5050 DL. This product has a mole percent composition of 50% lactide and 50% glycolide. Other suitable commercially available products are Medisorb 65:35 DL, 75:25 DL, 85:15 DL and poly(d,l-lactic acid) (d,l-PLA). Poly(lactide-co-glycolides) are also commercially available from Boerhinger Ingelheim (Germany) under its Resomer© mark, e.g., PLGA 50:50 (Resomer RG 502), PLGA 75:25 (Resomer RG 752) and d,l-PLA (resomer RG 206), and from Birmingham Polymers (Birmingham, Ala.). These copolymers are available in a wide range of molecular weights and ratios of lactic to glycolic acid.

Pharmaceutically acceptable polyanhydrides which are useful in the present invention have a water-labile anhydride linkage. The rate of drug release can be controlled by the particular polyanhydride polymer utilized and its molecular weight. The polyanhydride polymer may be branched or linear. Examples of polymers which are useful in the present invention include homopolymers and copolymers of poly (lactic acid) and/or poly(glycolic acid), poly[bis(p-carboxyphenoxy)propane anhydride] (PCPP), poly[bis(p-carboxy)methane anhydride] (PCPM), polyanhydrides of oligomerized unsaturated aliphatic acids, polyanhydride polymers prepared from amino acids which are modified to include an additional carboxylic acid, aromatic polyanhydride compositions, and co-polymers of polyanhydrides with other substances, such as fatty acid terminated polyanhydrides, e.g., polyanhydrides polymerized from monomers of dimers and/or trimers of unsaturated fatty acids or unsaturated aliphatic acids. Polyanhydrides may be prepared in accordance with the methods set forth in U.S. Pat. No. 4,757,128, hereby incorporated by reference. For example, polyanhydrides may be synthesized by melt polycondensation of highly pure dicarboxylic acid monomers converted to the mixed anhydride by reflux in acetic anhydride, isolation and purification of the isolated prepolymers by recrystallization, and melt polymerization under low pressure ($10^{-4}$ mm) with a dry ice/acetone trap at a temperature between 140° C.–250° C. for 10–300 minutes. High molecular weight polyanhydrides are obtained by inclusion of a catalyst which increases the rate of anhydride interchain exchange, for example, alkaline earth metal oxides such as CaO, BaO and $CaCO_3$. Polyorthoester polymers may be prepared, e.g., as set forth in U.S. Pat. No. 4,070,347, hereby incorporated by reference.

Proteinaceous polymers may also be used. Proteinaceous polymers and their soluble derivatives include gelation biodegradable synthetic polypeptides, elastin, alkylated collagen, alkylated elastin, and the like. Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alanine, L-lysine, L-phenylalanine, L-valine, L-tyrosine, and the like.

In embodiments where the biodegradable polymer comprises a gel, one such useful polymer is a thermally gelling polymer, e.g., polyethylene oxide, polypropylene oxide (PEO-PPO) block copolymer such as Pluronic® F127 from BASF Wyandotte. In such cases, the local anesthetic formulation may be injected via syringe as a free-flowing liquid, which gels rapidly above 30° C. (e.g., when injected into a patient). The gel system then releases a steady dose of local anesthetic at the site of administration.

In additional embodiments, the sustained release material, which in effect acts as a carrier for the local anesthetic and/or the augmenting agent, can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan.

Definitions or further descriptions of any of the foregoing terminology are well known in the art and may be found by referring to any standard biochemistry reference text such as "Biochemistry" by Albert L. Lehninger, Worth Publishers, Inc. and "Biochemistry" by Lubert Stryer, W.H. Freeman and Company, both of which are hereby incorporated by reference.

The aforementioned biodegradable hydrophobic and hydrophilic polymers are particularly suited for the methods and compositions of the present invention by reason of their characteristically low human toxicity and virtually complete biodegradability.

The substrates of the presently described formulations in certain preferred embodiments are manufactured using a method that evenly disperses the local anesthetic throughout the formulation, such as emulsion preparation, solvent casting, spray drying or hot melt, rather than a method such as compression molding. A desired release profile can be achieved by using a mixture of polymers having different release rates and/or different percent loading of local anesthetic and/or augmenting agent, for example, polymers releasing in one day, three days, and one week. In addition, a mixture of microspheres having one or more different local anesthetic agents, having the same or different controlled release profile, can be utilized to provide the benefits of different potencies and spectrum of activity during the course of treatment.

Methods for manufacture of microspheres are well known and are typified in the following examples. Examples of suitable methods of making microspheres include solvent evaporation, phase separation and fluidized bed coating.

In solvent evaporation procedures, the local anesthetic agent, if soluble in organic solvents, may be entrapped in the biodegradable polymer by dissolving the polymer in a volatile organic solvent, adding the drug to the organic phase, emulsifying the organic phase in water which contains less than 2% polyvinyl alcohol, and finally removing the solvent under vacuum to form discrete, hardened monolithic microspheres.

Phase separation microencapsulation procedures are suitable for entrapping water-soluble agents in the polymer to prepare microcapsules and microspheres. Phase separation involves coacervation of the polymer from an organic solvent by addition of a nonsolvent such as silicone oil. In a preferred embodiment, the microspheres may be prepared by the process of Ramstack et al., 1995, in published international patent application WO 95/13799, the disclosure of which is incorporated herein in its entirety. The Ramstack et al. process essentially provides for a first phase, including an active agent and a polymer, and a second phase, that are pumped through a static mixer into a quench liquid to form microparticles containing the active agent. The first and second phases can optionally be substantially immiscible and the second phase is preferably free from solvents for the polymer and the active agent and includes an aqueous solution of an emulsifier. In fluidized bed coating, the drug is dissolved in an organic solvent along with the polymer. The solution is then processed, e.g., through a Wurster air suspension coating apparatus to form the final microcapsule product.

The biodegradable sustained release materials may be used in order to prepare sustained release local anesthetic implants. The implants may be manufactured, e.g., by compression molding, injection molding, and screw extrusion, whereby the local anesthetic agent is loaded into the polymer. Implantable fibers can be manufactured, e.g., by blending the local anesthetic agent with the sustained release material and then extruding the mixture, e.g., under pressure, to thereby obtain biodegradable fibers. In certain preferred embodiments, the augmenting agent may be incorporated into the implant, or may be coated onto a surface of the implant.

In other embodiments of the invention, the sustained release material comprises an artificial lipid vesicle, or liposome. The use of liposomes as drug delivery systems is known, and comprehensive review articles on their properties and clinical applications are available; see, e.g., Barenholz and Amselem, in "Liposome Technology", 2nd ed., G. Gregoriadis, ed., CRC Press, 1992; Lichtenberg and Barenholz, in Methods for Biochemical Analysis, 33, D. Glick, ed., 1988. A liposome is defined as a structure consisting of one or more concentric lipid bilayers separated by water or aqueous buffer compartments. These hollow structures, which have an internal aqueous compartment, can be prepared with diameters ranging from 20 nm to 10 μm. They are classified according to their final size and preparation method as: SUV, small unilamellar vesicles (0.5–50 nm); LUV, large unilamellar vesicles (100 nm); REV, reverse phase evaporation vesicles (0.5 μm); and MLV, large multilamellar vesicles (2–10 μm).

Liposomes as described herein will vary in size. Preferably, the liposomes have a diameter between 100 nm and 10 microns or greater. A wide variety of lipid materials may be used to form the liposomes including natural lecithins, e.g., those derived from egg and soya bean, and synthetic lecithins, the proviso being that it is preferred that the lipids are non-immunogenic and biodegradable. Also, lipid-based materials formed in combination with polymers may be used, such as those described in U.S. Pat. No. 5,188,837 to Domb, (incorporated by reference herein).

Examples of synthetic lecithins which may be used together with their respective phase transition temperatures, are di-(tetradecanoy)phosphatidylcholine (DTPC) (23 C), di-(hexadecanoyl)phosphatidylcholine (DHPC) (41 C) and di-(octandecanoyl) phosphatidylcholine (DOPC) (55 C). Di-(hexadecanoyl) phosphatidylcholine is preferred as the sole or major lecithin, optionally together with a minor proportion of the di-(octadecanoyl) or the di-(tetradecanoyl) compound. Other synthetic lecithins which may be used are unsaturated synthetic lecithins, for example, di-(oleyl) phosphatidyl-choline and di-(linoleyl)phosphatidylcholine. In addition to the main liposome-forming lipid or lipids, which are usually phospholipids, other lipids (e.g. in a proportion of 5–40% w/w of the total lipids) may be included, for example, cholesterol or cholesterol stearate, to modify the structure of the liposome membrane, rendering it more fluid or more rigid depending on the nature of the main liposome-forming lipid or lipids.

In certain embodiments, the augmenting agent is incorporated along with the local anesthetic agent into the lipid. In other preferred formulations, the lipids containing the local anesthetic agent are dispersed in a pharmaceutically acceptable aqueous medium. The augmenting agent may be incorporated into this aqueous medium. In a further embodiment, a portion of the dose of the local anesthetic is incorporated into the aqueous medium in immediate release form. The resultant formulation is an aqueous suspension which may comprise the local anesthetic and/or augmenting agent partitioned between a free aqueous phase and a liposome phase.

As an even further alternate embodiment, liposomes containing local anesthetic may be combined in an aqueous phase where liposomes containing the augmenting agent form an aqueous pharmaceutical suspension useful for administration at the desired site in the patient to be anesthetized. This may be accomplished via injection or implantation. Liposomes may be prepared by dissolving an appropriate amount of a phospholipid or mixture or phospholipids together with any other desired lipid soluble components (e.g., cholesterol, cholesterol stearate) flowing in a suitable solvent (e.g., ethanol) and evaporating to dryness. An aqueous solution of the local anesthetic, optionally with augmenting agent, may then be added and mixed until a lipid film is dispersed. The resulting suspension will contain liposomes ranging in size, which may then fractionated to remove undesirable sizes, if necessary. This fractionation may be effected by column gel chromatography, centrifugation, ultracentrifugation or by dialysis, as well known in the art.

The above method of preparation of liposomes is representative of a possible procedure only. Those skilled in the art will appreciate that there are many different methods of preparing liposomes, all of which are deemed to be encompassed by the present disclosure.

In additional embodiments of the invention, the substrate comprises a plurality of microcapsules laden with the local anesthetic agent with or without the augmenting agent. Microcapsules may be prepared, for example, by dissolving or dispersing the local anesthetic agent in an organic solvent and dissolving a wall forming material (polystyrene, alkylcelluloses, polyesters, polysaccharides, polycarbonates, poly(meth)acrylic acid ester, cellulose acetate, hydroxypropylmethylcellulose phthalate, dibutylaminohydroxypropyl ether, polyvinyl butyral, polyvinyl formal, polyvinylacetaldiethylamino acetate, 2-methyl-5-vinyl pyridine methacrylate-methacrylic acid copolymer, polypropylene, vinylchloride-vinylacetate copolymer, glycerol distearate, etc.) in the solvent; then dispersing the solvent containing the local anesthetic agent and wall forming material in a continuous-phase processing medium, and then evaporating a portion of the solvent to obtain microcapsules containing the local anesthetic agent in suspension, and finally, extracting the remainder of the solvent from the microcapsules. This procedure is described in more detail in U.S. Pat. Nos. 4,389,330 and 4,530,840, hereby incorporated by reference.

The sustained release dosage forms of the present invention preferably provide a sustained action in the localized area to be treated. For example, it would be desirable that such a formulation provides localized anesthesia to the site for a period of one day, two days, three days, or longer. The formulations can therefore, of course, be modified in order to obtain such a desired result.

Microspheres and other injectable substrates described herein may be incorporating an effective amount of the same into a pharmaceutically acceptable solution (e.g., water) or suspension for injection. The final reconstituted product viscosity may be in a range suitable for the route of administration. In certain instances, the final reconstituted product viscosity may be, e.g., about 35 cps. Administration may be via the subcutaneous or intramuscular route. However, alternative routes are also contemplated, and the formulations may be applied to the localized site in any manner known to those skilled in the art, such that a localized effect is obtained. The substrate formulations of the invention can be implanted at the site to be treated. Thereby, the formulations of the present invention, when including a local anesthetic, may be used in the control of post-operative pain.

The local anesthetic is incorporated into the polymer or other sustained-release formulation in a percent loading between 0.1% and 90% or more, by weight, preferably between 5% and 80%, or more, by weight and more preferably between 65 and 80%, or more, by weight. In an even more preferred embodiment, the local anesthetic is loaded at about 75% by weight.

It is possible to tailor a system to deliver a specified loading and subsequent maintenance dose by manipulating the percent drug incorporated in the polymer and the shape of the matrix or formulation, in addition to the form of local anesthetic (e.g., free base versus salt) and the method of production. The amount of drug released per day increases proportionately with the percentage of drug incorporated into the formulation, e.g., matrix (for example, from 5 to 10 to 20%). In the preferred embodiment, polymer matrices or other formulations with about 75% drug incorporated are utilized, although it is possible to incorporate substantially more drug, depending on the drug, the method used for making and loading the device, and the polymer.

When the augmenting agent is included in the sustained release substrates (e.g., microparticles) comprising local anesthetic, it has been found that useful loadings of augmenting agent are from about 0.001% to about 30% by weight of the substrate or preferably from about 0.01% to about 5% by weight of the substrate. When the augmenting agent is included in sustained release substrates (e.g., microparticles) without local anesthetic, it has been found that useful loadings of augmenting agent are from about 0.001% to about 90%, or more, by weight of the substrate, or preferably from about 0.001% to about 30% by weight of the substrate or more preferably from about 0.01% to about 5% by weight of the substrate.

When the augmenting agent is included as part of the (aqueous) injection medium, the augmenting agent may be present in a weight percent relative to the local anesthetic varying from about 0.01% to about 15%.

The dosage of the sustained release microsphere formulations is dependent upon the kind and amount of the drug to be administered, the recipient animal, and the objectives of the treatment. For example, when the local anesthetic included in the microspheres of the present invention is bupivacaine, the formulation may include, e.g., from about 0.5 to about 2 mg/kg body weight. The effective dose of bupivacaine, or an amount of another local anesthetic sufficient to provide proportional potency, can range from about 1 to 50 mg of bupivacaine injected or inserted at each site where the release of a local anesthetic agent is desired. In certain preferred embodiments, the dose of bupivacaine in the sustained release dosage form of the invention is sufficient to provide a sustained release of about 1 to 4 mg per day at the release site for at least 1 to 4 days. Since the formulations of the present invention are sustained release, it is contemplated that formulations may include much more than usual immediate release doses, e.g., as much as 120 mg/kg bupivacaine or more.

In certain preferred embodiments, the sustained release substrate (e.g., microparticles) comprising local anesthetic and/or augmenting agent provides from about 10 to about 60 percent release of drug, e.g., local anesthetic after 24 hours, from about 20 to about 80 percent release after 48 hours and from about 40 to about 100 percent release after 72 hours. In such embodiments, it is preferred that the sustained release formulation provide anesthesia and/or local numbness and/or pain relief at the desired site for about 3–5 days. More preferably, the sustained release substrate comprising local anesthetic provides from about 25 to about 40 percent release of local anesthetic after 24 hours, from about 40 to about 50 percent release after 24 hours and from about 45 to about 55 percent release after 72 hours and 80 to 100 percent cumulative release is provided after about 280 hours. In such embodiments, it is preferred that the sustained release formulation provide anesthesia and/or local numbness and/or pain relief at the desired site for about 3–5 days.

In order to obtain a local anesthetic effect in-vivo when combined with the augmenting agent as described herein of at least about 40 hours the augmenting agent is placed into approximately the same site in a patient (e.g., human or veterinary) before, simultaneously with, or after the placement of a local anesthetic at that site. The presence of augmenting agent in the sustained release formulation does not significantly affect the in-vitro release rates of local anesthetic.

In a preferred embodiment the local anesthetic effect is prolonged by the use of an augmenting agent by at least about 15%, e.g., from about 15% to about 1400% or more preferably from about 300% to about 1000% or more and more preferably from about 300% to about 500%, or more of the duration of the local anesthetic effect that is obtained from the same formulation without benefit of an augmenting agent. The duration of the local anesthetic effect prolonged by an augmenting agent ranges from about 30 minutes to about 150 hours, or more, and preferably from 1 hour to about 1 to about 24 hours or more, and more preferably from about 1 hour to about 12 hours, or more.

The rate of release of local anesthetic agent or other drugs incorporated into the formulation will also depend on the solubility properties of the local anesthetic or drug. The greater the solubility in water, the more rapid the rate of release in tissue, all other parameters being unchanged. For example, those local anesthetic agents having pH dependent solubility will be released more rapidly at the optimum pH for those compounds. Thus, the formulation may be optimized for the desired local anesthetic release rate by selecting local anesthetic agents having a desired water solubility in tissue, e.g., at tissue pH. Thus, a local anesthetic agent that is more soluble at acid pH will have a faster release rate in a relatively acidic (e.g., pH less than about 7.2) tissue. For example, in one embodiment, the formulation will have released, in vitro, at least 70 percent of a local anesthetic at 48 hours at about pH 6 and will have released at least 40 percent of a local anesthetic at a pH ranging from about 7.4 to about 8, at 48 hours. Other combinations are pH independent in their release.

The examples demonstrate that the above-described augmenting agents prolong the duration of local anesthesia in-vivo and do not significantly alter the time course of release of bupivacaine in-vitro.

Applications

Potential applications include any condition for which intra articular sustained release of one or more of the active agents enumerated hereinabove is desirable. In a preferred embodiment, potential applications include any condition for which localized anesthesia and/or anti inflammatory activity is desirable. Preferably, the formulations according to the invention are inserted, injected, infiltrated or infused into an articular joint in need of local anesthesia, e.g., prevention or reduction of pain sensation. Thus, painful joints can be treated with local anesthetic having prolonged effect. Conditions to be treated by the formulations according to the invention include lower back pain, neck pain, including, e.g., whiplash pain in the affected joint or joints, e.g., the zygopohyseal joints, pain in the joints of the extremities such as knee and elbow joints caused by disease and/or by trauma.

In a preferred embodiment, the methods of the invention are particularly suited for the treatment of arthritic joint disease, e.g., rheumatoid arthritis where a combination of local anesthetic and a glucocorticosteroid antiinflammatory agent provides both immediate and prolonged local anesthetic activity, as well as the additional antiinflammatory activity when the glucocorticosteroid is administered in an amount effective for antiinflammatory activity.

In an especially preferred embodiment, the formulation according to the invention is in the form of a plurality of sustained release microparticles also referred to herein as extended duration local anesthetic (EDLA).

Of course, the aforementioned applications of the methods of the invention are merely mentioned as examples, and additional applications for both human and veterinary practice will be immediately apparent to the artisan.

The formulations of the invention are also suitable for administration in all body spaces/cavities, including but not limited to pleura, peritoneum, cranium, mediastinum, pericardium, bursae or bursal, epidural, intrathecal, intraocular, etc.

The uses of the formulations of the invention includes both local anesthesia for the relief of pain and motor symptoms as well as local anesthesia for other medical purposes. The formulations and methods according to the invention can be used to provide two to five day intercostal blockade for thoracotomy, or longer term intercostal blockade for thoracic post-therapeutic neuralgia, lumbar sympathetic blockade for reflex sympathetic dystrophy, or three-day ilioinguinal/iliohypogastric blockade for hernia repair. Other potential applications include obstetrical or gynecological procedures. Yet further potential applications include providing localized temporary sympathectomy, e.g., blockade of sympathetic or parasympathetic ganglia to treat a variety of autonomic diseases, including circulatory dysfunction or cardiac dysrhythmias. The formulations may also be used to treat trigeminal neuralgia and other diseases of the cranial nerves as well as to provide a temporary nerve block to treat localized muscle spasm and treatment of retrobulbar conditions, e.g., eye pain. Other uses include intra-operative administration in order to reduce pain during and after the operative procedure, especially for plastic surgery procedures where prolonged local anesthesia will enhance the outcome. These systems can also be used for the management of various forms of persistent pain, such as postoperative pain, sympathetically maintained pain, or certain forms of chronic pain such as the pain associated with many types of cancer. These systems may also be used for blockade of nociceptive pathways (afferent and efferent) in patients with acute pancreatitis, ileus, or other visceral disorders. These are merely examples, and additional uses for both human and veterinary practice are immediately apparent to one skilled in the art.

Methods of Administration

In a preferred method of administration an EDLA dosage form, e.g., microparticles such as microspheres or microcapsules, are administered by injection into a site where local anesthetic agent is to be released. Microspheres may be injected through a syringe or a trochar. Pellets, slabs or solid formulations shaped to fit particular locations, e.g., articular joints, may be surgically placed into a site where release of oral anesthetic agent is desired. Sustained release gels, pastes or suspensions, including gels, pastes or suspension containing microparticles, may also be administered topically to a skin or mucosal surface of the body to obtain topical, localized anesthesia. For treatment of joint pain of the back or neck the EDLA may be administered by intra articular injection into one or more facet joints.

As described below, microspheres according to the invention can be administered alone or in combination with a solution including a glucocorticoid or non-glucocorticosteroid augmenting agent in an amount effective to prolong the duration of local anesthesia. Alternatively, the microspheres include an amount of a non-glucocorticosteroid augment agent effective to prolong the duration of local anesthesia.

In another alternative, one or more augmenting agents can be administered before, simultaneously with or after administration of the sustained release local anesthetic, wherein the augmenting agent is formulated into a separate microsphere formulation for sustained release. The controlled release rate for the augmenting agents may be the same as or different than the controlled release rate for the local anesthetic. The separate microsphere can be administered in a single injection, i.e., in a single injection vehicle, or in separate injections simultaneously or at different times. In a further embodiment, it has been found that additional dose of augmenting agent may also be administered as an injectable solution, in an injectable carrier or in a sustained release carrier to the nerve to be blockaded after the sustained release local anesthesia has worn off, in order to reactivate the initial local anesthesia without the co-administration of additional local anesthetic.

The microspheres may be prepared from PLGA polymers ranging from, for example, PLGA in a ratio of 50/50, 65/35 or 75/25. An optimum composition has been determined to be PLGA 65/35. The microspheres, formulated with, e.g., PLGA 65/35 microspheres are administered in a dose ranging from, for example, 2 through 450 mg of microspheres 75% (w/w) loaded with a local anesthetic such as bupivacaine, per kg of the patient to be treated. In a preferred embodiment the dose ranges from 5 through 450 mg/kg. In a more preferred embodiment the dose ranges from about 10 to about 150 mg/kg with PLGA 65/35. Certainly, the artisan will appreciate the fact that the dose ranges mentioned above are based on the potency of bupivacaine, and that exact effective dosages will vary with the particular relative potency and pharmacokinetics of each local anesthetic and will be able to readily adjust the dose according to the degree of blockade experienced by the patient.

The use of the above-described augmenting agents before, simultaneously with or after administration of a sustained release local anesthesia, results in prolonged anesthesia.

A suspension of microspheres prepared in a form suitable for intra articular injection can be injected into a joint using methods well known to the art. For most body spaces, the use of a needle or "skinny needle" is acceptable. The chosen needle is one that is small in bore (large) gauge as possible, and as long as necessary. Commonly, for a joint, epidural, intraperitoneal, intrapleural or bursae, 22–28 gauge, 1–2 inch is used. For the microparticles used in the present invention, one should allow for increased bore size (e.g., to 18 gauge). This also allows for the puncturing needle to be removable, being encased in a plastic infusion catheter. For a few procedures, "skinny needles" are used. Such needles have the same bores but are longer, and hence look "skinny". For locations such as intrapericardial, the gauges for the skinny needle are the same, but the needles can be up to 3–4 inches long. For epidural, and other locations, there is a metal puncturing needle of the same gauges and up to 3 inches long, often encased in a plastic catheter, through which another catheter, fromm 22–28 gauge, and up to 6–12 inches long, can be inserted into the space.

DETAILED DESCRIPTION OF THE PREFERRED EMBODIMENTS

The following non-limiting examples illustrate the preparation of the formulations according to the invention and the effects of local anesthetic and augmenting agents alone and in combination.

EXAMPLES 1–3

Solvent Extraction Process

In Examples 1–3, bupivacaine microspheres are prepared by dissolving the bupivacaine base and the polymer in ethyl acetate. The polymer is 50:50 poly (D,L) lactic co-glycolic acid which has a mole percent composition of 50% lactide and 50% glycolide. This dispersed phase is then added to a solution of polyvinyl alcohol (PVA) in water (the continuous phase) with stirring. The resulting emulsion is monitored for droplet size, which is in turn controlled by the rate of stirring. The emulsion is then added to water to extract the solvent and to harden the microspheres. The mixture is then filtered and the microspheres are dried under vacuum at room temperature. The desired particle size fraction is then collected by sieving.

Each of Examples 1–3 are prepared such that the microspheres have a relatively high drug content. In Example 1, the theoretical drug content is about 60%, and the size of the microspheres range from about 45 to about 90 microns. In Example 2, the theoretical drug content is about 61%, and the range in the size of the microspheres is from about 45 to about 63 microns. In Example 3, the theoretical drug content is about 65%, and the range in particle size of the microspheres is from about 45 to about 63 microns.

The microspheres of Examples 1–3 are then suspended in a suitable media for injection, in this case water. Thereafter, the microspheres are subjected to in-vitro dissolution testing. An automated dissolution test method is utilized using the USP/NF Paddle Method II. The dissolution medium is 900 ml of Tris buffer with 0.05% sodium dodecyl sulfate at pH 7.4 at 37° C. with a stirring speed of about 50 RPM. The surfactant is added in order to prevent the microspheres from floating on the surface of the dissolution medium. Further information concerning these formulations is presented in Table 1 below.

TABLE 1

| Formulation | M-Sphere Size Range | Theoretical % Drug | Actual % Drug | MW of 50:50 dl-PLGA | In vitro Release | |
|---|---|---|---|---|---|---|
| | | | | | 24 hrs | 72 hrs |
| Ex. 1 | 45–90μ | 62% | 47% | — | 28% | 68% |
| Ex. 2 | 45–63μ | 61% | 56% | 50K | 52% | 91% |
| Ex. 3 | 45–63μ | 65% | 59% | 50K | 22% | 46% |

From the results set forth in Table 1, no correlation between drug content and release rate can be readily made.

It was expected that the formulation of Example 3 would release drug faster than that of Example 1 because of a higher drug content. However, the in-vitro release for Example 3 was slower than expected. It is hypothesized that this is due to the glass transition temperature of the polymer being lowered (below about 37° C.) by the high drug content. This situation may or may not be translated into in-vivo results.

EXAMPLES 4–9

Spray-dried

In Examples 4–9, the bupivacaine base and the polymer utilized in Examples 1–3 are once again dissolved in ethyl acetate, but this time the microspheres are obtained by spray-drying the solution. Example 4 utilizes a relatively high drug content, whereas Example 5 utilizes a relatively low drug content. In Examples 7–9, microspheres having a substantially similar drug content to Examples 4–5 are prepared using the solvent extraction technique utilized in Examples 1–3. Details of the formulations are presented in Table 2 below.

TABLE 2

| Formulation | Drug Content (Theoretical) | Yield | Process |
|---|---|---|---|
| Ex. 4 | 49% | 55% | Spray-Dried |
| Ex. 5 | 29% | 64% | Spray-Dried |
| Ex. 6 | 45% | — | Spray-Dried |
| Ex. 7 | 47% | 62% | Solvent Extraction |
| Ex. 8 | 28% | 74% | Solvent Extraction |
| Ex. 9 | 60% | 60% | Solvent Extraction |

With regard to Example 9, the actual percentage of bupivacaine base in the microspheres is 51%, the molecular weight of the 50:50 dl-PLGA polymer is 18,000, the microspheres were about 45–63 microns, and in-vitro dissolution conducted as in Examples 1–3 showed that 61% of the bupivacaine was released in 22 hours.

The microspheres of Examples 6 and 9 are suspended in a suitable injection medium (e.g., water) and then subjected to in-vitro dissolution testing via the procedures set forth in Examples 1–3. The in-vitro dissolution results are determined for 22 hours.

The in-vitro dissolutions of Examples 4–5 and 7–8 are determined as per the Examples above, and compared to the dissolution of the bupivacaine free base and the bupivacaine hydrochloride salt forms. When compared to pure bupivacaine base, each of Examples 4–5 and 7–8 showed a distinct retarding effect in their dissolution profile. Furthermore, all four examples of the invention displayed a small initial burst of drug release which was more pronounced in the microspheres prepared by the spray-dried process as compared to the examples prepared by the solvent extraction process.

Scanning electron micrographs of the microspheres for the formulations prepared by the solvent extraction and by the spray-dried technique are then compared. The spray-dried process yields microspheres which are smaller than with the solvent extraction process.

EXAMPLE 10

Local Anesthesia Induced by Sustained Release Microspheres is Prolonged by Co-Administration of Dextran Augmenting Agent in the Injection Solution Microspheres are prepared which contain 75% bupivacaine, by weight. The duration of local anesthesia induced by the bupivacaine-loaded microspheres, prepared from PLGA 65:35, with and without the co-administration of an augmenting agent, is tested in a rat sciatic nerve model for localized local anesthesia. In this procedure, groups of rats are selected that demonstrate normal behavior in a leg withdrawal latency test at least a week prior to the experimental procedure. The latency test determines the time, in seconds, before a rat withdraws its hindpaw from a hotplate set to a safe but uncomfortable temperature (56° C.).

Selected rats are injected with a solution containing a suspension of bupivacaine-loaded microspheres plus co-administered augmenting agent on one side and injected with a control on the contralateral side so that each rat serves as its own control. Each injection is adjacent to the sciatic nerve. The controls are bupivacaine-loaded microspheres without co-administered augmenting agent and microspheres without any bupivacaine.

A. Sensory Testing

As previously discussed, the degree of sensory local anesthesia is measured by determining the time or latency, in seconds, before each rat withdraws its hindpaw from a hotplate set to a safe but uncomfortable temperature. Maximum sciatic nerve sensory blockade is defined as having a latency of about 12 seconds or higher.

B. Motor Testing

The degree of motor blockade is measured by scoring the appearance of the affected foot for the signs of loss of motor tone. The assessment is conducted as follows using a 4-point scale based on visual observation: (1) normal appearance, (2) intact dorsiflexion of foot with an impaired ability to splay toes when elevated by the tail, (3) toes and foot remained plantar flexed with no splaying ability, and (4) loss of dorsiflexion, flexion of toes, and impairment of gait.

C. Experimental Protocol Twenty-four rats each receive an injection of bupivacaine-loaded sustained release microspheres into the left or right side, co-administered with a dextran containing injection solution. The contralateral side receive either bupivacaine-loaded microspheres at the same dose, or unloaded microspheres co-administered with a dextran injection solution.

Sensory hot plate latency is measured from the time of the injections until the latency declined to under 2 seconds.

Motor blockade is scored until the hind paws of motor blockades rats returned to a normal appearance.

The dose of bupivacaine contained in each sciatic nerve injection ranges from 5 to 450 mg/kg of rat or about 1.5 to 50 mg at each injection site.

The tested dextrans has a molecular weight ranging from 20 kDa through 200 kDa. The injection solution containing dextran is buffered to a pH ranging from 7.0 to 8.3.

D. Results

On the sides receiving co-administered dextran augmenting agent show a significantly longer duration of sensory block and significantly increased duration of motor block than do the sides receiving sustained-release bupivacaine-loaded microspheres without co-administered dextran. Unloaded microspheres with dextran alone produce no sensory blockade.

EXAMPLE 11

Local Anesthesia Induced by Sustained Release Microspheres is Prolonged by Co-Administration of Alkalinizing Agents in the Injection Solution Preparation of microspheres and testing procedures are as described above. In this experiment it is shown that co-administration of alkalinizing agents in the injection solution serve to significantly prolong the duration of local anesthesia induced by the injection of sustained release bupivacaine-loaded microspheres adjacent to rat sciatic nerve.

A. Experimental Protocol

Twenty-four rats each receive an injection of bupivacaine-loaded sustained release microspheres into the left or right side, adjacent to the sciatic nerve, in carbonate-buffered injection solution. The contralateral side receives either bupivacaine-loaded microspheres at the same dose at pH 7.4, or unloaded microspheres with the same injection buffer as the treatment side. The pH of the experimental injection solution ranges from pH 7.0 through pH 8.3.

B. Results

The degree of sensory and motor local anesthesia show a significant increase in duration proportional to the alkalinity of the carbonate-buffered injection solution, with the optimum results obtained as the pH approached 8.

EXAMPLE 12

Local Anesthesia Induced by Sustained Release Microspheres was Prolonged by Co-Administration of Agents with Diverse Pharmacological Activity In this example, a large number of pharmaceutical agents were tested for activity in augmenting the duration of local anesthetic activity. Bupivacaine-containing microspheres at about 75% loading, by weight, were injected perineurally into rat sciatic nerve at a dose of 150 mg/kg (weight microspheres/weight rat) to dose of approximately 50 mg/nerve. For the injections, needle placement adjacent to the target nerve was optimized by intermittent electrical e stimulation of the target nerve (via the injection needle) with low amplitude current to produce limb flexion. For the injections, the microspheres were suspended in a carrier vehicle suitable for injection. While any pharmaceutically acceptable carrier vehicle is acceptable, for these experiments the carrier vehicle was 1% sodium carboxymethyl-cellulose and 1% Tween 80 in water.

Compounds to be tested were co-injected with bupivacaine containing microspheres (i.e., mixed as additives into the carrier vehicle) in a range of concentrations. Results are expressed as percent increase in duration relative to non-augmented durations that were obtained in the same animal model.

The duration of anesthesia was measured by the hotplate foot withdrawal method described above in Example 10 and refers to the time necessary for the animal to recover from maximal nerve latency (12 sec) to a latency of 7 seconds, approximately 50% recovery. The results are tabulated in Table 3 below as percent of control.

TABLE 3

Efficacy of Additives to LAB As Percent of Control Without Additive

| Additive | % Additive Conc. | Duration Anesthesia As Percent of Control | Principle Pharmacological Activity of Additive |
|---|---|---|---|
| Allotetrahydrocortisone | 0.05 | 100 | Steroid, GABA receptor modulator |
| Allotetrahydrocortisone | 0.5 | 117 | |
| Alphaxalone | 0.05 | 169 | Steroid, GABA receptor modulator and anesthetic |
| Alphaxalone | 0.5 | 123 | |
| Aminopyridine (4-AP) | 0.05 | 77 | Potassium channel blocker |
| Aminopyridine (4-AP) | 0.11 | 92 | |
| Aminopyridine (4-AP) | 1.09 | 131 | |
| Aminopyrine | 0.05 | 146 | Analgesic |
| Aminopyrine | 0.5 | 62 | |
| Benzamil | 0.05 | 83 | Sodium channel inhibitor |
| Benzamil | 0.5 | 154 | |
| Clonidine | 0.05 | 122 | Partial 2 adrenergic agonist and vasoconstrictor. |
| Clonidine | 0.5 | 71 | |
| Colchicine | 0.01 | 104 | Microtubule inhibitor, inhibitor of glucose metabolism in leukocytes (among other properties). |
| Colchicine | 0.1 | 677, 1308 | |
| Colchicine | 1.0 | 277 | |
| Colchicine | 10 | toxic | |
| Colchicine (Placebo) | 0.1 | 0 | |
| Colchicine (no LAB) | 10 | 0 | |
| DehydroePiandrosterone | 0.05 | | Steroid, GABA receptor modulator |
| DehydroePiandrosterone | 0.5 | | |

TABLE 3-continued

Efficacy of Additives to LAB As Percent of Control Without Additive

| Additive | % Additive Conc. | Duration Anesthesia As Percent of Control | Principle Pharmacological Activity of Additive |
|---|---|---|---|
| Dextran | 3 | 146–144 | Osmotic polysaccharide |
| Dextran | 6 | Anesthesia continued past end of test period | |
| Diazepam | 0.05 | 231 | Modulates GABA receptor |
| Diazepam | 0.5 | 203 | |
| Diazoxide | 0.05 | 138 | Potassium-ATP channel agonist |
| Diazoxide | 0.5 | 109 | |
| 5,5-diphenylhydantoin | 0.05 | 145, 119 | Sodium channel inhibitor |
| 5,5-diphenylhydantoin | 0.11 | 152 | |
| 5,5-diphenylhydantoin | 1.09 | 138 | |
| Minoxidil | 0.05 | 54 | Potassium channel agonist |
| Minoxidil | 0.5 | 218–265 | |
| Ouabain | 0.05 | 154 | Na,K-ATPase inhibitor |
| Ouabain | 0.5 | 178 | |
| Spantide | 0.05 | 119 | Neurokinin antagonist |
| Spantide | 0.5 | 172 | |
| Taxol | 0.05 | 188, 138 | Microtubule assembly promoter |
| Taxol | 0.11 | 104 | |
| Taxol | 0.5 | 82 | |
| Taxol | 1.09 | 108 | |
| Tetraethylammonium | 0.05 | 95 | Potassium channel blocker |
| Tetraethylammonium | 0.5 | 123 | |
| U-73, 122* | 0.05 | 106 | PLC inhibitor |
| U-73, 122* | 0.5 | 115 | |
| Valproic Acid | 0.05 | 152 | Potassium channel opener |
| Valproic Acid | 0.5 | 138 | |
| Vinblastine | 0.05 | 158 | Microtubule inhibitor |
| Vinblastine | 0.11 | 37 | |
| Vinbiastine | 1.09 | 40 | |

* (1-[6-[[17-beta-3-methoxyestra-1,3,5(10)-triene-17-yl]amino]hexl]-1-H-pyrrole-2,5-dione)

EXAMPLE 13

Epinephrine as Augmenting Agent

Microspheres containing bupivacaine loaded to about 75 percent by weight with bupivacaine are prepared, with and without added epinephrine, in a percent loading of about 0.05 percent, by weight, using the methods described in Examples 1–3 or Examples 4–9, above.

Following the protocol set forth in Example 10, above, selected rats are injected adjacent to the sciatic nerve with a solution containing a suspension of bupivacaine-loaded microspheres on the right side, and on the left side with a solution containing a suspension of bupivacaine-loaded microspheres and also containing 0.05 percent epinephrine.

Sensory and motor testing is conducted according to sections A and B, respectively, of EXAMPLE 10, above. Using the experimental protocol of section C of EXAMPLE 10, 24 rats are tested.

On the sides receiving a combination of bupivacaine and epinephrine in sustained release microspheres, a significantly longer duration of sensory block and significantly increased duration of motor block was obtained than with the sides receiving sustained-release bupivacaine-loaded microspheres without sustained release epinephrine.

EXAMPLE 14

Amphetamine as Augmenting Agent

In experiments conducted according to EXAMPLE 13, above, amphetamine is substituted for epinephrine, with the same concentrations of each agent. On the sides receiving a combination of bupivacaine and amphetamine containing controlled release microspheres, a significantly longer duration of sensory block and significantly increased duration of motor block was obtained than with the sides receiving sustained-release bupivacaine-loaded microspheres without sustained release amphetamine.

EXAMPLE 15

Ephedrine as Augmenting Agent

Microspheres containing bupivacaine loaded to about 75 percent by weight with bupivacaine are prepared, in a percent loading of about 0.05 percent, by weight, using the methods described in EXAMPLES 1–3 or EXAMPLES 4–9, above. In addition, microspheres containing added ephedrine, in a percent loadings of 0.001 percent, 0.05 percent and 1 percent, without bupivacaine, are also prepared according to EXAMPLES 1–3 or EXAMPLES 4–9, above.

Following the protocol set forth in EXAMPLE 10, above, selected rats are injected adjacent to the sciatic nerve with a solution containing a suspension of bupivacaine-loaded microspheres on the right side, and on the left side with a solution containing a suspension of bupivacaine-loaded microspheres and also containing ephedrine containing microspheres in each dose level.

Sensory and motor testing is conducted according to sections A and B, respectively, of EXAMPLE 10, above. Using the experimental protocol of section C of EXAMPLE 10, 24 rats are tested for each of the three ephedrine dose levels by injecting ephedrine-containing microspheres (same number of microspheres per rat, adjusted for animal weight) at about the same time as the bupivacaine-containing microspheres are administered. On the sides receiving a combination of bupivacaine microspheres and epedrine microspheres, a significantly longer duration of sensory block and significantly increased duration of motor block was obtained than with the sides receiving sustained-release bupivacaine-loaded microspheres without sustained release ephedrine for each dose level, with the effect showing a dose-response curve according to concentration.

EXAMPLE 16

In-vivo Injection into Joints

As can be appreciated, a substantial range of pharmaceutical agents is capable of augmenting the duration of local anesthetic activity. In addition, these compounds were tested as additives in the vehicle suspending the microspheres. Including an augmenting agent into the sustained release formulation itself is expected to substantially improve the prolongation of local anesthetic activity by prolonging the presence of augmenting agent at the anesthetized site.

EDLA (Extended Duration Local Anesthetic), as the term is used in this example, is a formulation of bupivacaine and dexamethasone in a matrix of poly(lactide:glycolide) 65:35 microspheres, which releases the bupivacaine and dexamethasone over a period of several days. The polymer is also biodegradable, and remnants may last for several weeks to months. The formulation used in this study consisted of about 72% bupivacaine and 0.04% dexamethasone by mass, the microspheres ranging in size from about 25 $\mu$m–125 $\mu$m, with a mass median diameter of just over 100 $\mu$m.

Local anesthetics have been previously injected into joint spaces to relieve pain, with mixed results. The present formulation has been demonstrated to provide anesthesia having a duration of several days in a number of animal species. However, in order to confirm that the EDLA in the form of microparticles does not cause mechanical damage when administered to joint spaces that are freely exercising, the following experiments were conducted.

Method of Manufacture 50 mg of poly(lactide:glycolide) ("PLGA") 65:35 (High molecular weight) and 150 mg of bupivacaine free base (obtained from Purdue-Frederick) were dissolved in 0.1 ml of a solution of 5 mg of dexamethasone in 5 mls in $CH_2Cl_2$ and 0.9 mls of $CH_2Cl_2$. 1 ml of 0.3% polyvinyl alcohol (PVA) in 100 mM Tris buffer at pH 8.5 was added and the mixture vortexed 3 times for 15 seconds each time. The mixture was poured into 100 mls of 0.1% PVA in 100 mM Tris buffer. The microspheres were examined using the light microscope and the size distribution was determined, using a coulter counter, to be between 10 and 110 microns. The $CH_2Cl_2$ was removed by heating the sample to 31° C. using a rotary evaporator at full vacuum for 15 minutes. The suspension of microspheres in 0.1% PVA was filtered through 140, 60, and 20$\mu$ metal sleeves (Neward Wire Cloth Co.). Then the microspheres were frozen in liquid nitrogen and lyophilized overnight.

The EDLA microspheres composed of 72% bupivacaine, 0.04% dexamethasone, in poly(lactide:glycolide) (65:35) microspheres, mass median diameter of about 110 $\mu$m, were suspended in a vehicle of 0.5% sodium carboxymethylcellulose and 0.1% Tween 80 in water. All percentages are reported as weight percent unless otherwise specified.

Animals

The experiment was performed using three elderly male baboons that had previously been used in abdominal surgery studies, and which were scheduled to be sacrificed.

Protocol

The objective of the experiment was to inject EDLA microparticles into the knee joints of adult baboons and measure plasma concentrations of bupivacaine for several days, observe the movements of the animals for several days for induced lameness, physically examine the joints weekly for evidence of inflammation, and necropsy the animals and examine the joints grossly and histologically for lesions. Two animals received an injection of EDLA microspheres in one knee and vehicle in the other, while one animal received an injection of vehicle in one knee and no injection in the other knee (Table 4). The protocol was conducted in the following sequence.

Week 1, the animals were on a sham tether.

Week 2, the animals were on a tether.

Week 3, the knee joints were X-rayed and EDLA microspheres (bupivacaine and dexamethasone) were injected intra articularly.

During weeks 4, 5 and 6 serum drug levels, daily observations of walking were taken and physical examinations of the joints were conducted weekly. Final X-rays and necropsy was conducted at day 21.

TABLE 4

| | Administration of Test Substances | |
|---|---|---|
| Animal | Joint space | Test substance |
| A | Left knee | EDLA, 70 mg in 1 ml |
| | Right knee | Vehicle, 1 ml |
| B | Left knee | Vehicle, 1 ml |
| | Right knee | EDLA, 70 mg in 1 ml of vehicle |
| C | Left knee | No injection |
| | Right knee | Vehicle, 1 ml |

The animals were tethered so that frequent blood samples could be drawn during the first week after injection to measure plasma bupivacaine. Radiographs were taken prior to the injection of the test article and three weeks after injection (prior to necropsy) for evidence of lesions. The radiograph (X-rays) were confirmed by pathology studies, including gross and histologic evaluations.

B. Results

1. In-life Observations

No evidence of inflammation, tenderness or altered range of motion on weekly physical examination of knees, in any animal.

2. Plasma Bupivacaine

Figure 2:
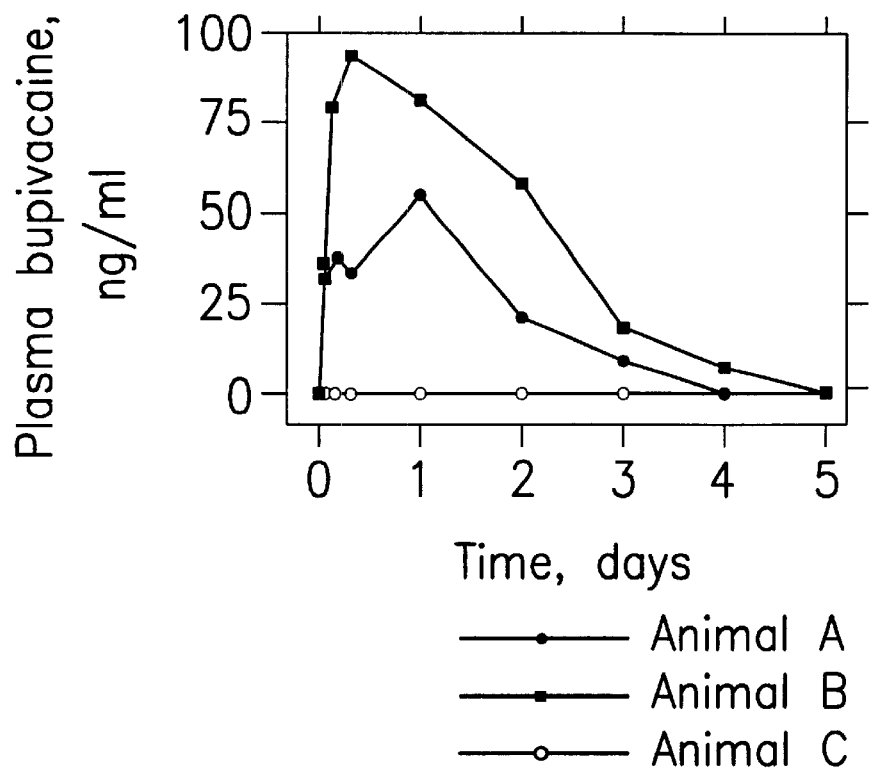
FIG. 2 charts the presence of plasma bupivacaine in each of three test animals after the injection of EDLA in the form of bupivacaine-containing microspheres.

FIG. 2 is a graph which depicts the presence of plasma bupivacaine after the administration of the EDLA bupivacaine microspheres.

As shown in FIG. 2, Animal A, who was injected with 70 mg of the EDLA in the left knee, had over 75 ng/ml plasma bupivacaine during day 1. Thereafter the level of bupivacaine decreased to approximately 60 ng/ml after day 2, and below 25 ng/ml after day 3, until the level reached 0 ng/ml after day 5.

Animal B, who was injected with 70 mg of the EDLA in the right knee had over 50 ng/ml plasma bupivacaine after day 1. Thereafter the level of bupivacaine decreased to 25 ng/ml after day 2 until the level reached 0 ng/ml after day 4.

FIG. 2 confirms that Animal C, who was not injected with the EDLA, had no plasma bupivacaine during the days of the study.

3. Gross Observations on Necropsy

Joints were examined for swelling, warmth, and discoloration. All were negative. Range of motion and ease of motion were evaluated and all were judged normal. Joint capsule fluid was examined for transparency, color, and cells. All were negative. The joint capsule was examined for swelling and thickening, and for discoloration. All were negative. The cartilaginous surfaces of the medial femur, lateral femur, medial tibia, lateral tibia, medial meniscus, and lateral meniscus were examined for roughness. All were judged normal.

4. Histopathologic Observations

The histopathological evaluations were conducted in a blinded manner.

Gross evaluation criteria were as follows.

Motion, mobility.

Inflammation was scored on a scale of 0–3 based on the observation of swelling, temperature and color.

Capsule fluid was scored on a scale of 0–3 based on transparency, bloody and purulent.

Joint capsule was scored on a scale of 0–3 based on swelling and color.

Cartilaginous surfaces were scored on a scale of 0–3, each, at the medical femur, lateral femur, media tibia, lateral tibia, medial meniscus, lateral meniscus.

Results

All specimens were graded as "0".

Animal A: (EDLA, left knee): Giant cell formation around foreign material was evident in the synovial membrane of the left knee, with minimal lymphocyte infiltration around the giant cells. Cartilaginous surfaces were normal. Cartilage and synovial membrane was normal in the right knee. Diagnosis was listed:

Granulomatous arthritis, minimal, left knee.

Animal B: (EDLA, right knee): Giant cell formation around foreign material was evident in the synovial membrane of the right knee, with minimal lymphocyte infiltration around the giant cells. Cartilaginous surfaces were normal. Cartilage and synovial membrane was normal in the left knee. Diagnosis was listed:

Granulomatous arthritis, minimal, right knee.

Animal C (diluent, right knee): The cartilaginous surfaces and synovial membranes were normal in both knees.

C. Conclusions

Injection of EDLA microspheres into the knee joints of normal baboons resulted in no damage to articulating surfaces when assessed after three weeks. EDLA particles were trapped in synovial membrane, with minimal foreign body reactions as a consequence. This type of reaction has been observed to EDLA and other microsphere formulations in most other studies. The incorporation of dexamethasone in EDLA microspheres results in an attenuated response; further increase in glucocorticosteroid concentration in EDLA microspheres may result in even less inflammation, and may itself provide a therapeutic benefit in osteoarthritic joints.

Thus, the local tissue concentration of bupivacaine maintained by the EDLA microsphere formulation mirrors the observation that the local anesthesia produced by EDLA microspheres provides rapid onset and prolonged duration of action.

EXAMPLE 17

In-vivo Intraperitoneal Administration

In Example 17, a study was undertaken to examine intraperitoneal administration to rats. The goal of this exercise was to administer EDLA into another "cavity," the intraperitoneal cavity. The biological effect studied was inhibition of gastrointestinal motility as reflected by increased transit time through the small intestine. EDLA (low molecular weight polymer) was utilized in this study, and was prepared by forming an oil-in-water emulsion from an aqueous solution containing a surfactant (process water) and an organic solvent (oil) solution containing drug and polymer. Following emulsification, the solvent was removed in an aqueous quench allowing the microspheres to harden. Details are as follows:

Materials

Process water (aqueous phase) was prepared as follows: A 1% stock solution of polyvinylalcohol (PVA) was prepared by the addition of 30 g PVA (Spectrum) to 3.0 L of deionized water and heated while mixing to 65–70° C. until dissolved. The PVA solution was cooled to ambient temperature and q.s. to 3.0 L. Next, 375 ml of the stock PVA solution was diluted with 1125 ml of deionized water. Finally, 90 ml (80.1 g) of ethyl acetate NF (Fisher) was stirred into the process water prior to forming the emulsion.

The polymer/drug solution (organic phase) was prepared as follows: 5.6 g of Medisorb 65:35DL PLGA (inherent viscosity=0.34 dl/g) was dissolved in 150 ml (133.5 g) of ethyl acetate NF under ambient conditions. Next, 0.011 g dexamethasone (Upjohn) was added. Then, 14.4 g of bupivacaine base (Orgamol) was added to the polymer solution and sonicated until dissolved. Finally, the organic phase was filtered through a 0.22 µm PTFE filter. The quench solution consisted of 8 L of deionized water at RT.

The organic phase and the aqueous phase were pumped simultaneously through a ½" diameter by 21 element static mixer (Cole Parmer) to form an emulsion. The organic phase was pumped at a rate of 500 ml/minute and the aqueous phase at 1000 ml/minute, into the quench solution, which was being stirred mechanically (500 rpm). The quench solution was then stirred for 1.5 hour, after which the product was passed through 125 and 25 µm sieves. The 25–125 µm portion was collected on 10 µm filter paper and dried 4 hours under vaccuum followed by air drying overnight. The process yield was 11.27 g of bupivacaine/dexamethasone-loaded microspheres (EDLA).

Method

Charcoal, 10% in gum acacia, 5%, 0.25 ml, was administered to CD-1 mice by gavage. After 20 minutes, animals were euthanized using $CO_2$. The gastrointestinal tract was removed, beginning with the stomach, carefully dissecting the mesentery to avoid stretching the small intestine, with transection at the ileocolic junction. The tract was measured from the jejunopyloric junction to the ileocolic junction. Finally, the distance traveled by the charcoal meal was measured. Gastrointestinal transit was quantitated as the percentage the meal traveled through the tract compared to the overall length of the tract.

In the trial experiment, a dose of EDLA (low molecular weight polymer), 50 mg in 0.3 ml, was administered 4 hours prior to the charcoal meal. In animals receiving vehicle, transit was 68±2%, n=10, compared to 43±4%, n=10 in the animals receiving EDLA, t=5.66, df=18, p<0.0001.

EXAMPLE 18

In-vivo Epidural Injection

In Example 18, the methods and procedures of Example 16 are repeated, except that the formulation is instead used for epidural administration. For epidural administration, a catheter is inserted, either for an acute administration or indwelling for chronic administration. The dose per administration should be 10–150 mg equivalent of bupivacaine, which is the maximum approved for the aqueous formulation. However, by virtue of the formulations used in the present disclosure, it has been demonstrated that such formulations are up to 40 times more safe than such approved formulations; therefore, it is possible that the dose of bupivacaine can be 40 times greater than the 10–150 mg equivalent cited above. The vehicle is the same used in other applications: sodium carboxymethylcellulose —0.05%; polysorbate 80— 0.1%; mannitol—50 mM; pH 7.4. The EDLA microspheres are diluted so that administration yields the desired bupivacaine dose in the desired volume (10 mg—greater than 150 mg) in 2 ml to 50 ml.

The examples provided above are not meant to be exclusive. Many other variations of the present invention would be obvious to those skilled in the art, and are contemplated to be within the scope of the appended claims. Numerous publications are cited herein, the disclosures of which are incorporated herein by reference in their entireties.

What is claimed is:

1. A method of treating localized pain, comprising administering a formulation into a body space selected from the group consisting of pleura, peritoneum, cranium, mediastinum, pericardium, bursae, epidural space, intrathecal space, and intraocular space, said formulation comprising (a) a local anesthetic incorporated in an effective amount of a biocompatible, biodegradable sustained release material, which prolongs the release of the local anesthetic from the formulation, and (b) a non-toxic augmenting agent in an amount effective to prolong the effect of the local anesthetic in-vivo, to treat pain arising from said body space.

2. A method of treating localized pain, comprising administering a formulation into a body space selected from the group consisting of pleura, peritoneum, cranium, mediastinum, pericardium, bursae, epidural space, intrathecal space, and intraocular space, said formulation comprising (a) controlled release microparticles comprising a local anesthetic and an effective amount of a biocompatible, biodegradable sustained release polymer selected from polyanhydrides, copolymers of lactic acid and glycolic acid, poly(lactic) acid, poly(glycolic) acid, polyesters, polyorthoesters, proteins, polysaccharides and combinations thereof and (b) a non-toxic augmenting agent in an amount effective to prolong the effect of the local anesthetic in-vivo, said formulation when administered providing pain relief to said body space, said formulation when administered in-vivo providing local anesthesia or analgesia or numbness or pain relief for at least about 24 hours.

3. The method of claim 1, wherein the formulation further comprises a second active agent selected from an enzyme, an anti-infective agent, an antibody, a diagnostic aid, a radio-opaque dye, a magnetic resonance imaging dye, a radiolabeled agent, and combinations thereof.

4. The method of claim 2, wherein said bursae is selected from the group consisting of acromial, bicipitoradial, cubitoradial, deltoid, infrapatellar, ishchiadica, and any other bursae subject to pain.

5. The method of claim 3, wherein at least a portion of said second active agent is incorporated into said microparticles.

6. The method of claim 1, wherein the local anesthetic is bupivacaine, the augmenting agent is dexamethasone, and the sustained release material is a poly(lactide co-glycolide).

7. The method of claim 2, wherein said formulation when administered in-vivo provides local anesthesia or analgesia or numbness or pain relief for at least about 3–5 days.

8. The method of claim 2, wherein at least a portion of said augmenting agent is incorporated into said microparticles.

9. The method of claim 2, wherein said augmenting agent is a glucocorticosteriod.

10. The method claim 2, wherein said microparticles comprise local anesthetic in a percent loading between 65 and 80%, and said augmenting agent is a glucocorticosteroid present in a weight percent relative to the local anesthetic from 0.005% to 15%.

11. The method of claim 9, wherein said glucocorticosteriod is selected from the group consisting of dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone, and mixtures thereof.

12. The method of claim 2, wherein a plurality of said microparticles are suspended in a pharmaceutically acceptable vehicle for injection.

13. The method of claim 2, wherein said local anesthetic is selected from the group consisting of bupivacaine, ropivacaine, dibucaine, etidocaine, tetracaine, lidocaine, xylocaine, mixtures thereof, and salts thereof.

14. A method of treating localized pain arising from a body space in a mammal, comprising injecting a formulation into a body space selected from the group consisting of pleura, peritoneum, cranium, mediastinum, pericardium, bursae, epidural space, intrathecal space, and intraocular space, said formulation comprising a pharmaceutically acceptable medium containing a plurality of microspheres comprising a local anesthetic and an effective amount of a biocompatible, biodegradable controlled release material capable of degrading at least fifty percent in less than two years following injection of the formulation in vivo, said controlled release material being selected from the group consisting of polyanhydrides, copolymers of lactic acid and glycolic acid, poly(lactic) acid, poly(glycolic) acid, polyesters, polyorthoesters, proteins, polysaccharides and combinations thereof, said formulation further comprising a non-toxic augmenting agent which is (i) incorporated into and/or onto said microspheres; or (ii) incorporated into said pharmaceutically acceptable medium, or (iii) incorporated into said microspheres and also incorporated into said pharmaceutically acceptable medium; said microspheres being included in said formulation in an amount sufficient to obtain reversible local anesthesia or analgesia or numbness or pain relief or anti-inflammatory effect for at least about 24 hours when said formulation is injected into said body space.

15. The method of claim 14, wherein said augmenting agent is a glucocorticosteriod.

16. A method of prolonging the effect of a local anesthetic agent in body spaces, comprising injecting a formulation into a body space selected from the group consisting of pleura, peritoneum, cranium, mediastinum, pericardium, bursae, epidural space, intrathecal space, and intraocular space, said formulation comprising a pharmaceutically acceptable medium containing a plurality of microspheres comprising a local anesthetic and an effective amount of a biocompatible, biodegradable controlled release material, said biocompatible, biodegradable controlled release material capable of degrading at least fifty percent in less than two years following injection of the formulation in vivo, said controlled release material being selected from the group consisting of polyanhydrides, copolymers of lactic acid and glycolic acid, poly(lactic) acid, poly(glycolic) acid, polyesters, polyorthoesters, proteins, polysaccharides and combinations thereof,
said formulation further comprising a non-toxic augmenting agent which is (i) incorporated into and/or onto said microspheres; or (ii) incorporated into said pharmaceutically acceptable medium, or (iii) incorporated into said microspheres and also incorporated into said pharmaceutically acceptable medium; said microspheres being included in said formulation in an amount sufficient to obtain reversible local anesthesia or analgesia or numbness or pain relief or anti-inflammatory effect for at least about 24 hours when said formulation is injected into said body space.

17. The method of claim 16, wherein said local anesthetic is selected from the group consisting of bupivacaine, ropivacaine, dibucaine, etidocaine, tetracaine, lidocaine, xylocaine, mixtures thereof, and salts thereof.

18. The method of claim 16, wherein said formulation when administered in-vivo provides local anesthesia or analgesia or numbness or pain relief for at least about 3 to about 5 days.

19. The method claim 16, wherein said microspheres are microcapsules.

20. The method of claim 16, wherein the diameter of the microspheres ranges in size from about 5 microns to about 200 microns.

21. The method of claim 16, wherein at least a portion of said local anesthetic is incorporated in said microspheres.

22. The method of claim 16, wherein said augmenting agent is a glucocorticosteriod.

23. A method of prolonging the effect of a local anesthetic agent in body spaces, comprising administering a formulation into a body space selected from the group consisting of pleura, peritoneum, cranium, mediastinum, pericardium, bursae, epidural space, intrathecal space, and intraocular space, said formulation comprising (a) controlled release microparticles comprising a local anesthetic and an effective amount of a biocompatible, biodegradable sustained release polymer selected from polyanhydrides, copolymers of lactic acid and glycolic acid, poly(lactic) acid, poly(glycolic) acid, polyesters, polyorthoesters, proteins, polysaccharides and combinations thereof; and (b) a non-toxic augmenting agent in an amount effective to prolong the effect of the local anesthetic in-vivo, for providing pain relief to a body space selected from the group consisting of pleura, peritoneum, cranium, mediastinum, pericardium, bursae, epidural space, intrathecal space, and intraocular space, said bursae selected from the group consisting of acromial, bicipitoradial, cubitoradial, deltoid, infrapatellar, and ishchiadica, and said formulation when administered in-vivo provides local anesthesia or analgesia or numbness or pain relief for at least about 24 hours.

24. The method of claim 23, wherein said augmenting agent is a glucocorticosteriod.

25. A method of treating localized pain, comprising administering a formulation into an intra-articular joint selected from the group consisting of knee, elbow, hip, sternoclavicular, temporomandibular, carpal, tarsal, wrist, ankle, and any other joint subject to pain, said formulation comprising (a) a local anesthetic incorporated in an effective amount of a biocompatible, biodegradable sustained release material, which prolongs the release of the local anesthetic from the formulation, and (b) a non-toxic augmenting agent in an amount effective to prolong the effect of the local anesthetic in-vivo, to treat pain arising from said intra-articular joint.

26. The method of claim 25, wherein said augmenting agent is a glucocorticosteriod.

27. A method of treating localized pain, comprising administering a formulation into a space selected from the group consisting of a pleural space, mediastinum, and pericardium, said formulation comprising (a) a local anesthetic incorporated in an effective amount of a biocompatible, biodegradable sustained release material, which prolongs the release of the local anesthetic from the formulation, and (b) a non-toxic augmenting agent in an amount effective to prolong the effect of the local anesthetic in-vivo, to treat pain arising from said space.

28. A method of treating localized pain, comprising administering a formulation into a space selected from the group consisting of a pleural space, mediastinum, and pericardium, said formulation comprising (a) controlled release microparticles comprising a local anesthetic and an effective amount of a biocompatible, biodegradable sustained release polymer selected from polyanhydrides, copolymers of lactic acid and glycolic acid, poly(lactic) acid, poly(glycolic) acid, polyesters, polyorthoesters, proteins, polysaccharides and combinations thereof; and (b) a non-toxic augmenting agent in an amount effective to prolong the effect of the local anesthetic in-vivo, said formulation when administered providing pain relief to said space, said formulation when administered in-vivo providing local anesthesia or analgesia or numbness or pain relief for at least about 24 hours.

29. A method of treating localized pain arising from a space in a mammal, comprising injecting a formulation into a space selected from the group consisting of a pleural space, mediastinum, and pericardium, said formulation comprising a pharmaceutically acceptable medium containing a plurality of microspheres comprising a local anesthetic and an effective amount of a biocompatible, biodegradable controlled release material capable of degrading at least fifty percent in less than two years following injection of the formulation in vivo, said controlled release material being selected from the group consisting of polyanhydrides, copolymers of lactic acid and glycolic acid, poly(lactic) acid, poly(glycolic) acid, polyesters, polyorthoesters, proteins, polysaccharides and combinations thereof, said formulation further comprising a non-toxic augmenting agent which is (i) incorporated into and/or onto said microspheres; or (ii) incorporated into said pharmaceutically acceptable medium, or (iii) incorporated into said microspheres and also incorporated into said pharmaceutically acceptable medium; said microspheres being included in said formulation in an amount sufficient to obtain reversible local anesthesia or analgesia or numbness or pain relief or anti-inflammatory effect for at least about 24 hours when said formulation is injected into said space.

30. A method of prolonging the effect of a local anesthetic agent in spaces, comprising injecting a formulation into a space selected from the group consisting of a pleural space, mediastinum, and pericardium, said formulation comprising a pharmaceutically acceptable medium containing a plurality of micro spheres comprising a local anesthetic and an effective amount of a biocompatible, biodegradable controlled release material, said biocompatible, biodegradable controlled release material capable of degrading at least fifty percent in less than two years following injection of the formulation in vivo, said controlled release material being selected from the group consisting of polyanhydrides, copolymers of lactic acid and glycolic acid, poly(lactic) acid, poly(glycolic) acid, polyesters, polyorthoesters, proteins, polysaccharides and combinations thereof, said formulation further comprising a non-toxic augmenting agent which is (i) incorporated into and/or onto said microspheres; or (ii) incorporated into said pharmaceutically acceptable medium, or (iii) incorporated into said microspheres and also incorporated into said pharmaceutically acceptable medium; said microspheres being included in said formulation in an amount sufficient to obtain reversible local anesthesia or analgesia or numbness or pain relief or anti-inflammatory effect for at least about 24 hours when said formulation is injected into said space.

31. A method of prolonging the effect of a local anesthetic agent in spaces, comprising administering a formulation into a space selected from the group consisting of a pleural space, mediastinum, and pericardium, said formulation comprising (a) controlled release microparticles comprising a local anesthetic and an effective amount of a biocompatible, biodegradable sustained release polymer selected from polyanhydrides, copolymers of lactic acid and glycolic acid, poly(lactic) acid, poly(glycolic) acid, polyesters, polyorthoesters, proteins, polysaccharides and combinations thereof; and (b) a non-toxic augmenting agent in an amount effective to prolong the effect of the local anesthetic in-vivo, for providing pain relief to a space selected from the group consisting of a pleural space, mediastinum, and pericardium, and said formulation when administered in-vivo provides local anesthesia or analgesia or numbness or pain relief for at least about 24 hours.

\* \* \* \* \*